US008114979B2

(12) United States Patent
Laikhter et al.

(10) Patent No.: US 8,114,979 B2
(45) Date of Patent: Feb. 14, 2012

(54) DI-ALPHA AMINO ANTHRAQUINONE COMPOSITIONS

(75) Inventors: Andrei Laikhter, Iowa City, IA (US); Mark Aaron Behlke, Coralville, IA (US); Yawfui Yong, Iowa City, IA (US); Scott Rose, Coralville, IA (US); Lingyan Huang, Coralville, IA (US)

(73) Assignee: Integrated DNA Technologies, Inc., Skokie, IL (US)

( * ) Notice: Subject to any disclaimer, the term of this patent is extended or adjusted under 35 U.S.C. 154(b) by 0 days.

(21) Appl. No.: 12/853,755

(22) Filed: Aug. 10, 2010

(65) Prior Publication Data

US 2011/0060150 A1 Mar. 10, 2011

Related U.S. Application Data

(62) Division of application No. 10/666,998, filed on Sep. 19, 2003, now Pat. No. 7,803,536.

(60) Provisional application No. 60/412,215, filed on Sep. 20, 2002.

(51) Int. Cl.
 C07H 21/04 (2006.01)
 C07C 45/27 (2006.01)
(52) U.S. Cl. ........................ 536/24.3; 552/208
(58) Field of Classification Search ............... None
 See application file for complete search history.

(56) References Cited

U.S. PATENT DOCUMENTS

| | | | |
|---|---|---|---|
| 2,264,303 | A | 12/1941 | Dickey |
| 3,218,309 | A | 11/1965 | Elslager et al. |
| 3,407,189 | A | 10/1968 | Merian |
| 3,970,617 | A | 7/1976 | Bruno |
| 4,358,535 | A | 11/1982 | Falkow et al. |
| 4,439,356 | A | 3/1984 | Khanna et al. |
| 4,683,194 | A | 7/1987 | Saiki et al. |
| 4,683,195 | A | 7/1987 | Mullis et al. |
| 4,683,202 | A | 7/1987 | Mullis |
| 4,711,955 | A | 12/1987 | Ward et al. |
| 4,820,630 | A | 4/1989 | Taub |
| 4,868,103 | A | 9/1989 | Stavrianopoulos et al. |
| 4,868,105 | A | 9/1989 | Urdea et al. |
| 4,889,818 | A | 12/1989 | Gelfand et al. |
| 4,914,210 | A | 4/1990 | Levenson et al. |
| 4,954,630 | A | 9/1990 | Klein et al. |
| 4,996,143 | A | 2/1991 | Heller et al. |
| 5,011,769 | A | 4/1991 | Duck et al. |
| 5,108,892 | A | 4/1992 | Burke et al. |
| 5,124,246 | A | 6/1992 | Urdea et al. |
| 5,188,934 | A | 2/1993 | Menchen et al. |
| 5,210,015 | A | 5/1993 | Gelfand et al. |
| 5,214,136 | A * | 5/1993 | Lin et al. ............ 514/44 A |
| 5,272,259 | A | 12/1993 | Claussen et al. |
| 5,304,645 | A | 4/1994 | Klein et al. |
| 5,312,728 | A | 5/1994 | Lizardi et al. |
| 5,326,679 | A | 7/1994 | Yanagisawa et al. |
| 5,328,824 | A | 7/1994 | Ward et al. |
| 5,451,463 | A | 9/1995 | Nelson et al. |
| 5,455,157 | A | 10/1995 | Hinzpeter et al. |
| 5,487,972 | A | 1/1996 | Gelfand et al. |
| 5,492,806 | A | 2/1996 | Drmanac et al. |
| 5,502,177 | A | 3/1996 | Matteucci et al. |
| 5,512,667 | A | 4/1996 | Reed et al. |
| 5,514,785 | A | 5/1996 | Van Ness et al. |
| 5,525,464 | A | 6/1996 | Drmanac et al. |
| 5,556,752 | A | 9/1996 | Lockhart et al. |
| 5,696,251 | A | 12/1997 | Arnold, Jr. et al. |
| 5,801,155 | A | 9/1998 | Kutyavin et al. |
| 5,804,375 | A | 9/1998 | Gelfand et al. |
| 5,824,796 | A | 10/1998 | Petrie et al. |
| 5,830,653 | A | 11/1998 | Froehler et al. |
| 5,846,726 | A | 12/1998 | Nadeau et al. |
| 5,849,482 | A | 12/1998 | Meyer, Jr. et al. |
| 5,876,930 | A | 3/1999 | Livak et al. |
| 5,942,610 | A | 8/1999 | Nelson et al. |
| 5,952,202 | A | 9/1999 | Aoyagi et al. |
| 6,007,992 | A | 12/1999 | Lin et al. |
| 6,028,183 | A | 2/2000 | Lin et al. |
| 6,114,518 | A | 9/2000 | Pitner et al. |
| 6,117,973 | A | 9/2000 | Batz et al. |
| 6,117,986 | A | 9/2000 | Nardone et al. |
| 6,214,979 | B1 | 4/2001 | Gelfand et al. |
| 6,312,894 | B1 | 11/2001 | Hedgpeth et al. |

(Continued)

FOREIGN PATENT DOCUMENTS

DE 2546535 4/1977

(Continued)

OTHER PUBLICATIONS

Mori et al., Oligodeoxynucleotide analogs with 5'-linked anthraquinone, vol. 249, No. 2, 213-218, FEB 07194, Jun. 1989.*
Miyashita et al., Synthesis and properties of novel antisense oligonucleotides bearing an anthraquinone moiety at an internucleotide linkage, Nucleic Acids Symposium, 1999, Series No. 42, pp. 163-164.*
Kuball et al.., Helical Twisting Power of Chiral Mono- and Bis-aminoanthraquinones,J. Mater. Chem., 1995, 5(12), 2167-2174.*
Boturyn, D. et al., "Synthesis of fluorescent probes for the detection of abasic sites in DNA," Tetrahedron (1997) 53 (15):5485-5492.
Ito, T. et al., "Reductive electron injection into duplex DNA by aromatic amines," J. Am. Chem. Soc. (2004) 126:15552-15559.

(Continued)

Primary Examiner — Mark Staples
(74) Attorney, Agent, or Firm — Michael Best & Friedrich LLP

(57) ABSTRACT

The invention provides novel anthraquinone compositions that are useful as broad-spectrum quenchers of fluorescence and provides methods for making and using them. The anthraquinone quenchers can be conjugated to a variety of biologically relevant compounds, including lipids, nucleic acids, polypeptides, and more specifically antigens, steroids, vitamins, drugs, haptens, metabolites, toxins, environmental pollutants, amino acids, peptides, proteins, nucleotides, oligonucleotides, polynucleotides, carbohydrates, and their analogs. The invention also provides kits comprising, in one or more containers, at least one anthraquinone quencher dye composition of the present invention, and instructions for using that composition.

6 Claims, 4 Drawing Sheets

U.S. PATENT DOCUMENTS

| | | | |
|---|---|---|---|
| 6,316,610 | B2 | 11/2001 | Lee et al. |
| 6,323,337 | B1 | 11/2001 | Singer et al. |
| 6,399,392 | B1 | 6/2002 | Haugland et al. |
| 6,416,953 | B1 | 7/2002 | Heller |
| 6,441,159 | B1 | 8/2002 | Lukhtanov et al. |
| 6,448,407 | B1 | 9/2002 | Lee et al. |
| 6,451,535 | B1 | 9/2002 | Jenne et al. |
| 6,465,175 | B2 | 10/2002 | Horn et al. |
| 6,465,644 | B1 | 10/2002 | Yan et al. |
| 6,485,901 | B1 | 11/2002 | Gildea et al. |
| 6,531,581 | B1 | 3/2003 | Nardone et al. |
| 6,531,589 | B1 | 3/2003 | Iyer et al. |
| 6,531,591 | B1 | 3/2003 | Fensholdt |
| 6,653,473 | B2 | 11/2003 | Reed et al. |
| 6,699,975 | B2 | 3/2004 | Reed et al. |
| 6,727,356 | B1 | 4/2004 | Reed et al. |
| 6,790,945 | B2 | 9/2004 | Lukhtanov et al. |
| 6,800,728 | B2 | 10/2004 | Schwartz |
| 6,825,331 | B2 | 11/2004 | Manoharan et al. |
| 6,875,858 | B1 | 4/2005 | DeFrancq et al. |
| 7,122,383 | B2 | 10/2006 | Jones et al. |
| 7,173,125 | B2 | 2/2007 | Schwartz et al. |
| 7,439,341 | B2 | 10/2008 | Laikhter et al. |
| 7,476,735 | B2 | 1/2009 | Laikhter et al. |
| 7,605,243 | B2 | 10/2009 | Laikhter et al. |
| 7,645,872 | B2 | 1/2010 | Laikhter et al. |
| 2002/0034754 | A1 | 3/2002 | Reed et al. |
| 2002/0137070 | A1 | 9/2002 | Elghanian et al. |
| 2003/0082547 | A1 | 5/2003 | Ewing et al. |
| 2003/0096254 | A1 | 5/2003 | Reed et al. |
| 2003/0144499 | A1 | 7/2003 | McGall et al. |
| 2004/0110308 | A1 | 6/2004 | Laikhter et al. |
| 2004/0180343 | A1 | 9/2004 | Weber |
| 2007/0218490 | A1 | 9/2007 | Laikhter et al. |
| 2009/0053821 | A1 | 2/2009 | Laikhter et al. |
| 2010/0076181 | A1 | 3/2010 | Laikhter et al. |

FOREIGN PATENT DOCUMENTS

| | | |
|---|---|---|
| EP | 0070685 | 1/1983 |
| EP | 0070686 | 1/1983 |
| EP | 0070687 | 1/1983 |
| EP | 0152886 | 8/1985 |
| EP | 0185494 | 6/1986 |
| EP | 0246864 | 11/1987 |
| EP | 0272007 | 6/1988 |
| EP | 0320308 | 6/1989 |
| EP | 0357011 | 3/1990 |
| EP | 0439182 | 7/1991 |
| GB | 1394368 | 5/1975 |
| GB | 1533121 | 11/1978 |
| JP | 52-88681 | 7/1977 |
| JP | 52-91031 | 8/1977 |
| WO | WO 89/09284 | 10/1989 |
| WO | WO 89/10979 | 11/1989 |
| WO | WO 90/14353 | 11/1990 |
| WO | WO 91/05060 | 4/1991 |
| WO | WO 92/10588 | 6/1992 |
| WO | WO 96/17957 | 6/1996 |
| WO | WO 96/28460 | 9/1996 |
| WO | WO 96/34983 | 11/1996 |
| WO | 96/40662 | 12/1996 |
| WO | WO 97/29154 | 8/1997 |
| WO | WO 97/39008 | 10/1997 |
| WO | WO 99/14226 | 3/1999 |
| WO | WO 99/37717 | 7/1999 |
| WO | WO 99/40226 | 8/1999 |
| WO | WO 99/51621 | 10/1999 |
| WO | WO 99/51775 | 10/1999 |
| WO | WO 99/64431 | 12/1999 |
| WO | WO 00/06771 | 2/2000 |
| WO | WO 00/70685 | 11/2000 |
| WO | WO 01/04129 | 1/2001 |
| WO | WO 01/42505 | 6/2001 |
| WO | WO 01/86001 | 11/2001 |
| WO | WO 2004/026804 | 4/2004 |
| WO | WO 2004/113562 | 12/2004 |
| WO | WO 2005/049849 | 6/2005 |
| WO | WO 2006/127507 | 4/2007 |

OTHER PUBLICATIONS

United States Patent Office Action for U.S. Appl. No. 12/252,721 dated Oct. 15, 2010 (9 pages).

Canadian Patent Office Action for Application No. 2498320 dated Mar. 25, 2011 (3 pages).

7th International Symposium, held 2001, pp. 1-14, 7th International Symposium & Exhibition Solid Phase Synthesis & Combinatorial Chemical Libraries, Sep. 18 to 22, 2001—University of Southampton, England, UK.

Conference Proceedings, retrieved 2010, two pages, Innovation and Perspectives in Solid Phase Synthesis & Combinatorial Libraries: Peptides, Proteins and Nucleic Acids—Small Molecule Organic Chemistry Diversity, Collected Papers, International Symposium, 7th, Southampton, United Kingdom, Sep. 18-22, 2001, Roger Epton, Editor.

Easy Q&Q PCR, http://www.eurogentec.be/code/en/product_easy_qq.htm, visited May 9, 2002, 4 pages.

Encyclopedia Britannica (2008) "Nucleic Acid," Encyclopedia Britannica Online (Jul. 11, 2008) http://www.search.eb.com/eb/article-256731.

Genbank Accession No. AF298116, Rose et al., "Mus musculus bHLH protein Ptfl-p48 gene," (2001) 6 pages.

Gibson, V. et al., "Molecular modelling of anthraquinone-oligodeoxynucleotide conjugates," Pharm. Sci. (1996) 2:545-548.

Gorelick, M.V. et al., "Effect of benzannelation on the coloration of p-aminoazo compounds," Zhurnal Organicheskoi Khimii (1980) 16(9):1927-1933—Abstract only—Accession No. 1981:193676.

Greene, T.W. and Wuts, P.G.M., *Protective Groups in Organic Synthesis*, (1999) 3rd Ed. John Wiley & Sons, Inc., U.S. (Book Not Provided).

Haugland, R.P. et al., *Handbook of Flourescent Probes and Research Chemicals*, (1992) 5th Ed. Molecular Probes, Inc., Oregon, U.S. (Book Not Provided).

Ho, M.S. et al., "Azo polymers for reversible optical storage. 7. The effect of the size of the photochromic groups," Macromolecules (1995) 28(18):6124-6127 (Abstract only—Accession No. 1995:746851).

Hugentobler, M. et al., "Compounds with a metal-arene σ-bond. Part 2. Cyclometalation of arylazo compounds. Part 2. Regioselectivity of the cyclopalladation of some substituted 1-arylazonaphthalenes," Helvetica Chimica Acta (1982) 65(4):1202-1211 (Abstract only—Accession No. 1982:616430).

Jenkins, J.H., Senior Librarian at the United States Patent and Trademark Office, email dated Mar. 18, 2010 and previously related email corespondence, pp. 1-2.

Ju, J. et al., "Fluorescence energy transfer dye-labeled primers for DNA sequencing and analysis," Proc. Natl. Acad. Sci. USA (1995) 92:4347-4351.

Kerzhner, B.K. et al., "Photoisomerization of aromatic azo compounds adsorbed on a hydroxylated surface," Zhurnal Obshchei Khimii (1983) 53(10):2303-2306 (Abstract only—Accession No. 1984:50840).

Marshall, "Rules for the visible absorption spectra of halogenated fluorescein dyes," Histochemical J. (1975) 7:299-303.

May, J.P. et al., "A new dark quencher for use in genetic analysis," Chem. Commun. (2003) 970-971.

May, J.P. et al., "A novel dark quencher for oligonucleotide probes: synthesis and applications," poster presentation from TIDES 2002 IBC Oligonucleotide and Peptide Technology Conference, May 6-8, 2002, Las Vegas, Nevada (2 pages).

May, J.P. et al., "Synthesis of a novel dark quencher for use with long wavelength dyes in oligonucleotide probes," Innovation and Perspectives in Solid Phase Synthesis & Combinatorial Libraries: Peptides, Proteins and Nucleic Acids Small Molecule Organic Chemical Diversity, Collected Papers, 7th International Symposium, Southampton, United Kingdom, Sep. 18-22, 2002, 231-233.

Miyashita, T. et al., "Novel dinucleoside phosphotriester unit conjugated with an intercalative moiety in a stereospecific manner enhances thermal stability of an alternate-stranded triple helix," Tetrahedron Letters (2003) 44:7399-7402.

Mori, K. et al., "Oligodeoxynucleotide analogs with 5'-linked anthraquinone," FEBS Letters (1989) 249(2):213-218.

Morier-Teissier, E. et al., "Free radical production and DNA cleavage by copper chelating peptide-anthraquinones," Anti-Cancer Drug Design (1990) 5:291-305.

Mullis, K. et al., "Specific Enzymatic Amplification of DNA In Vitro: The Polymerase Chain Reaction," Cold Spring Harbor Symp. Quant. Biol. (1986) 51:263-273.

PR Newswire, Announcing IBC's TIDES 2002: Oligonucleotide and Peptide Technology Conferences May 6-8, 2002, Las Vegas, NV, Copyright 2002, PR Newswire Association LLC, pp. 1-2, website (retrieved Mar. 18, 2010): http://www.thefreelibrary.com/_/print/PrintArticle.aspx?id=82059345.

Puskas, L.G. et al., "Diamino-Antraquinone: A New Intercalating Agent. Synthesis and Linking to Oligodeoxynucleotide," Nucleosides & Nucleotides (1995) 14(3-5):967-968.

Rose, S.D. et al., "The Role of PTF1-P48 in pancreatic acinar gene expression," J. Biol. Chem. (2001) 276(47):44018-44026.

Schuster, G.B., "Long-range charge transfer in DNA: transient structural distortions control the distance dependence," Acc. Chem. Res. (2000) 33:253-260.

Zielske, A.G., "(Tosyloxy)anthraquinones: Versatile Synthons for the Preparation of Various Aminoanthraquinones," J. Org. Chem. (1987) 52:1305-1309.

Australian Patent Office Action for Application No. 2003275018 dated Aug. 11, 2008 (2 pages).

European Patent Office Supplementary Search Report for Application No. 03759288 dated Aug. 22, 2007 (6 pages).

European Patent Office Action for Application No. 03759288 dated Feb. 27, 2009 (4 pages).

European Patent Office Action for Application No. 03759288 dated Mar. 6, 2008 (6 pages).

International Preliminary Report on Patentability for Application No. PCT/US04/37932 dated Nov. 16, 2006 (8 pages).

International Search Report and Written Opinion for Application No. PCT/US04/37932 dated Jul. 28, 2006 (10 pages).

International Preliminary Report on Patentability for Application No. PCT/US03/029324 dated May 28, 2004 (4 pages).

International Search Report for Application No. PCT/US03/029324 dated Feb. 6, 2004 (1 page).

Japanese Patent Office Action for Application No. 2004-537958 dated Sep. 28, 2009 (11 pages) with English translation.

United States Office Action for U.S. Appl. No. 10/987,608 dated Mar. 28, 2008 (8 pages).

United States Office Action for U.S. Appl. No. 10/987,608 dated Oct. 5, 2007 (7 pages).

United States Office Action for U.S. Appl. No. 10/666,998 dated Jan. 8, 2008 (14 pages).

United States Office Action for U.S. Appl. No. 10/666,998 dated Jul. 16, 2008 (9 pages).

United States Office Action for U.S. Appl. No. 10/666,998 dated Jan. 16, 2009 (18 pages).

United States Office Action for U.S. Appl. No. 10/666,998 dated Sep. 17, 2009 (10 pages).

United States Patent Notice of Allowance for U.S. Appl. No. 10/666,998 dated Jan. 25, 2010 (12 pages).

United States Patent Office Action for U.S. Appl. No. 10/666,998 dated Jul. 1, 2010 (8 pages).

Agrawal, S. et al., "Efficient methods for attaching non-radioactive labels to the 5' ends of synthetic oligodeoxyribonucleotides," Nuc. Acids Res. (1986) 14:6227-6245.

Austermann, S. et al., "Inhibition of human immunodeficiency virus type 1 reverse transcriptase by 3'-blocked oligonucleotide primers," Biochem. Pharm. (1992) 43(12):2581-2589.

Bollum, F.J., "Oligodeoxyribonucleotide-primed reactions catalyzed by calf thymus polymerase," J. Bio. Chem. (1962) 237(6):1945-1949.

Cardullo, R.A et al., "Detection of nucleic acid hybridization by nonradiative fluorescence resonance energy transfer," Proc. Natl. Acad. Sci. USA (1988) 85:8790-8794.

Dey, S. and Sheppard, T.L., "Ketone-DNA: a versatile postsynthetic DNA decoration platform," Org. Lett. (2001) 3(25):3983-3986.

Gelfand, D.H., "Taq DNA Polymerase," PCR Technology Principles and Applications for DNA Amplification, Stockton Press, NY, Ehrlich ed. (1989) Ch. 2, 17-22.

Heesemann, J., "Studies on monolayers. 1. Surface tension and absorption spectroscopic measurements of monolayers of surface-active azo and stilbene dyes," J. Am. Chem. Soc. (1980) 102(7):2167-2176.

Heller, M.J. et al., "Chemiluminescent and fluorescent probes for DNA hybridization systems," Rapid Detection and Identification of Infectious Agents (1985) Academic Press, Inc., Orlando, Kingsbury et al. eds. 245-256.

Iyer, R.P. et al., "3H-1,2-benzodithiole-3-one 1,1-dioxide as an improved sulfurizing reagent in the solid-phase synthesis of oligodeoxyribonucleoside phosphorothioates," J. Am. Chem. Soc. (1990) 112:1253-1254.

Lawyer, F.C. et al., "Isolation, characterization, and expression in Escherichia coli of the DNA polymerase gene from thermus aquaticus," J. Biol. Chem. (1989) 264(11):6427-6437.

Lehman, I.R. et al., "Persistence of deoxyribonucleic acid polymerase I and its 5' →3' exonuclease activity in PolA mutants of Escherichia coli K12," J. Biol. Chem. (1973) 248(22):7717-7723.

Matthews, J.A. et al., "Analytical strategies for the use of DNA probes," Analy. Biochem. (1988) 169:1-25.

Misiura, K. et al., "Biotinyl and phosphotyrosinyl phosphoramidite derivatives useful in the incorporation of multiple reporter groups on synthetic oligonucleotides," Nucleic Acids Research (1990) 18(15):4345-4354.

Morrison, L.E. et al., "Solution-phase detection of polynucleotides using interacting fluorescent labels and competitive hybridization," Anal. Biochem. (1989) 183:231-244.

Noble, S.A. et al, "Methylphosphonates as probes of protein-nucleic acid interactions," Nuc. Acids Res. (1984) 12(7):3387-3404.

Proudnikov, D. et al., "Chemical methods of DNA and RNA fluorescent labeling," Nucleic Acids Res. (1996) 24(22):4535-4542.

Setlow, P. et al., "Deoxyribonucleic acid polymerase: two distinct enzymes in one polypeptide," J. Biol. Chem. (1972) 247(1):224-231.

Sijm, D.T.H.M. et al., "Aqueous solubility, octanol solubility, and octanol/water partition coefficient of nine hydrophobic dyes," Envir. Toxic. Chem. (1999) 18(6):1109-1117.

Telser, J. et al., "Synthesis and characterization of DNA oligomers and duplexes containing covalently attached molecular labels: comparison of biotin, fluorescein, and pyrene labels by thermodynamic and optical spectroscopic measurements," J. Am. Chem. Soc. (1989) 111:6966-6967.

Tu, C-P.D. et al., "3'-end labeling of DNA with [α-32P]cordycepin-5'-triphosphate," Gene (1980) 10:177-183.

European Patent Office Action for Application No. 03759288.8 dated Jul. 26, 2010 (4 pages).

International Search Report and Written Opinion for Application No. PCT/US06/19552 dated Dec. 27, 2006 (9 pages).

Japanese Patent Office Action for Application No. 2004-537958 dated Jul. 12, 2010 (5 pages) with English translation.

United States Patent Office Action for U.S. Appl. No. 12/252,721 dated Apr. 30, 2010 (10 pages).

United States Patent Office Action for U.S. Appl. No. 12/623,811 dated Feb. 17, 2010 (5 pages).

United States Patent Office Notice of Allowance for U.S. Appl. No. 12/252,721 dated Aug. 24, 2011 (6 pages).

United States Patent Office Notice of Allowance for U.S. Appl. No. 12/853,741 dated Jun. 16, 2011 (2 pages).

United States Patent Office Action for U.S. Appl. No. 12/252,721 dated Apr. 20, 2011 (7 pages).

United States Patent Office Action for U.S. Appl. No. 12/853,741 dated Nov. 26, 2010 (5 pages).

US 6,255,052, 05/2001, Batz et al. (withdrawn)

\* cited by examiner

Probe            Sequence

Seq ID No. 27     Cy5-ACCCGTTCACCCTCCCCAG-UQ2

DI-ALPHA AMINO ANTHRAQUINONE COMPOSITIONS

CROSS-REFERENCE TO RELATED APPLICATIONS

This application is a divisional of U.S. patent application Ser. No. 10/666,998 filed Sep. 19, 2003, which claims the benefit of U.S. Provisional Application No. 60/412,215 filed Sep. 20, 2002, both of which are incorporated herein by reference in their entirety.

FIELD OF THE INVENTION

This invention pertains to anthraquinone compositions that are useful as broad-spectrum quenchers of fluorescence and to methods for making and using them. The invention also provides kits that contain at least one of the disclosed anthraquinone quencher dye compositions.

BACKGROUND OF THE INVENTION

Chemical moieties that quench fluorescent light operate through a variety of mechanisms, including fluorescence resonance energy transfer (FRET) processes and ground state quenching. FRET is one of the most common mechanisms of fluorescent quenching and can occur when the emission spectrum of the fluorescent donor overlaps the absorbance spectrum of the quencher and when the donor and quencher are within a sufficient distance known as the Forster distance. The energy absorbed by a quencher can subsequently be released through a variety of mechanisms depending upon the chemical nature of the quencher. Captured energy can be released through fluorescence or through nonfluorescent mechanisms, including charge transfer and collisional mechanisms, or a combination of such mechanisms. When a quencher releases captured energy through nonfluorescent mechanisms FRET is simply observed as a reduction in the fluorescent emission of the fluorescent donor.

Although FRET is the most common mechanism for quenching, any combination of molecular orientation and spectral coincidence that results in quenching is a useful mechanism for quenching by the compounds of the present invention. For example, ground-state quenching can occur in the absence of spectral overlap if the fluorophore and quencher are sufficiently close together to form a ground state complex.

Quenching processes that rely on the interaction of two dyes as their spatial relationship changes can be used conveniently to detect and/or identify nucleotide sequences and other biological phenomena. For example, the change in fluorescence of the fluorescent donor or quencher can be monitored as two oligonucleotides (one containing a donor and one containing a quencher) bind to each other through hybridization. Advantageously, the binding can be detected without separating the unhybridized from the hybridized oligonucleotides.

Alternatively, a donor and quencher can be linked to a single oligonucleotide such that there is a detectable difference in fluorescence when the oligonucleotide is unhybridized as compared to when it is hybridized to its complementary sequence. For example, a self-complementary oligonucleotide designed to form a hairpin can be labeled with a fluorescent donor at one end and a quencher at the other end. Intramolecular annealing can bring the donor and quencher into sufficient proximity for FRET and fluorescence quenching occurs. Intermolecular annealing of such an oligonucleotide to a target sequence disrupts the hairpin, thereby increasing the distance between the donor and quencher, and resulting in an increase in the fluorescent signal of the donor.

Oligonucleotides labeled in a similar manner can also be used to monitor the kinetics of PCR amplification. In one version of this method the oligonucleotides are designed to hybridize to the 3' side ("downstream") of an amplification primer so that the 5'-3' exonuclease activity of a polymerase digests the 5' end of the probe and cleaves off a dye (either the donor fluorophore or quencher) from that end. The fluorescence intensity of the sample increases and can be monitored as the probe is digested during the course of amplification.

Similar oligonucleotide compositions find use in other molecular/cellular biology and diagnostic assays, such as in end-point PCR, in situ hybridizations, in vivo DNA and RNA species detection, single nucleotide polymorphism (SNPs) analysis, enzyme assays, and in vivo and in vitro whole cell assays.

As noted previously, the energy transfer process requires overlap between the emission spectrum of the fluorescent donor and the absorbance spectrum of the quencher. This complicates the design of probes because not all potential quencher/donor pairs can be used. For example, the quencher BHQ-1, which maximally absorbs light in the wavelength range of about 500-550 nm, can quench the fluorescent light emitted from the fluorophore fluorescein, which has a wavelength of about 520 nm. In contrast, the quencher BHQ-3, which maximally absorbs light in the wavelength range of about 650-700 nm would be less effective at quenching the fluorescence of fluorescein but would be quite effective at quenching the fluorescence of the fluorophore Cy5 which fluoresces at about 670 nm. The use of varied quenchers complicates assay development because the purification of a given probe can vary greatly depending on the nature of the quencher attached.

Many quenchers emit energy through fluorescence reducing the signal to noise ratio of the probes that contain them and the sensitivity of assays that utilize them. Such quenchers interfere with the use of fluorophores that fluoresce at similar wavelength ranges. This limits the number of fluorophores that can be used with such quenchers thereby limiting their usefulness for multiplexed assays which rely on the use of distinct fluorophores in distinct probes that all contain a single quencher.

Thus, new compositions are needed that quench fluorescence over a broad spectrum of wavelengths such that a single quencher can be used with a broad range of fluorophores. Ideally, such quenchers will not fluoresce so that the background fluorescence of probes is minimized giving such probes the potential to be more sensitive and more useful in multiplexed assays. The ideal quenchers should also have physical properties that facilitate their purification and the purification of probes into which they are incorporated. Such quenchers should also be chemically stable so that they can be incorporated into biological probes and used in assays without significant degradation. Ideally, such probes will be suitable for direct use in the synthesis of DNA oligomers so that oligonucleotides can be synthesized to contain them, as opposed to chemically adding the quencher to an oligonucleotide postsynthetically. Nevertheless, the quenchers should contain suitable reactive moieties to provide for their convenient incorporation into biologically relevant compounds such as lipids, nucleic acids, polypeptides, and more specifically antigens, steroids, vitamins, drugs, haptens, metabolites, toxins, environmental pollutants, amino acids, peptides, proteins, nucleotides, oligonucleotides, polynucleotides, carbohydrates, and the like. Lastly, the most useful compositions should be easily manufactured.

The invention provides nonfluorescing compositions with strong fluorescence quenching properties that function over a surprisingly wide wavelength range. Consequently, the disclosed compositions exhibit lower fluorescent backgrounds than quenchers that quench light at certain wavelengths and emit fluorescence at nearby wavelengths. Moreover, the anthraquinone quenchers of the present invention can be easily manufactured and purified. The compositions can be incorporated into biologically relevant compounds and, in many cases, impart useful purification properties to these compounds. These and other advantages of the invention, as well as additional inventive features, will be apparent from the description of the invention provided herein.

BRIEF SUMMARY OF THE INVENTION

The invention provides novel anthraquinone compositions that are useful as broad-spectrum quenchers of fluorescence and methods for making and using them. The anthraquinone quenchers can be conjugated to a variety of biologically relevant compounds, including lipids, nucleic acids, polypeptides, and more specifically antigens, steroids, vitamins, drugs, haptens, metabolites, toxins, environmental pollutants, amino acids, peptides, proteins, nucleotides, oligonucleotides, polynucleotides, carbohydrates, and their analogs. The invention also provides kits comprising, in one or more containers, at least one anthraquinone quencher dye composition of the present invention, and instructions for using that composition.

DETAILED DESCRIPTION OF THE INVENTION

Figure 1:
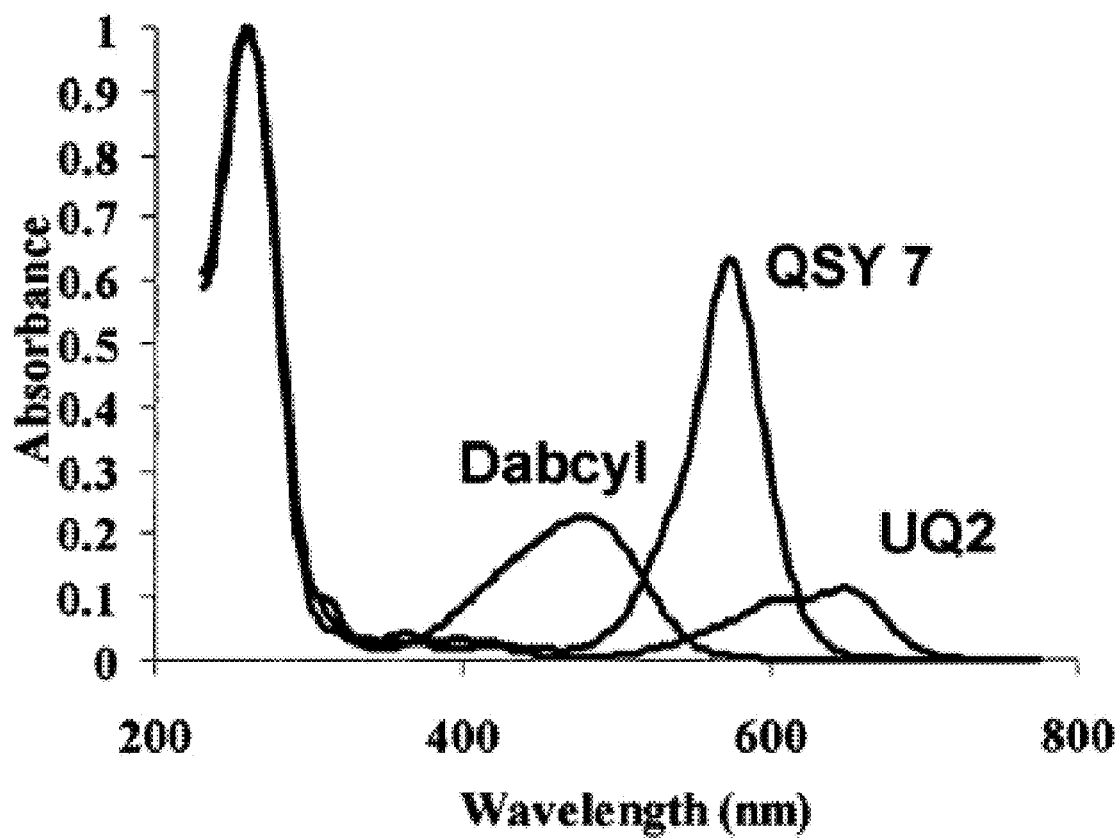
FIG. 1 shows the absorbance spectra of identical 12 nucleotide long oligonucleotides that contain quenchers conjugated to the 3' end. Oligonucleotides containing the anthraquinone quencher UQ2 (SEQ ID No: 1), and the quenchers QSY7 (SEQ ID No: 2), and Dabcyl (SEQ ID No: 3) were synthesized as described in Example 16.

The present invention stems, in part, from the discovery that the anthraquinone class of molecules, including 1,4-diamino anthraquinone compounds, have surprisingly strong quenching properties. These quenchers also overlap and efficiently quench fluorescence of a surprisingly wide wavelength range of emitted fluorescent light. Advantageously, they do not fluoresce. Consequently, they generally exhibit lower fluorescent backgrounds than quenchers that quench light at certain wavelengths and emit fluorescence over a wavelength range that bleeds into the fluorescent wavelength range of the reporter dye.

The anthraquinone quenchers of the present invention are easily purified. In certain instances a single purification using reverse phase HPLC chromatography provides highly pure compound. For example, the present quenchers can be incorporated into oligonucleotide probes and used in a variety of applications, including for example PCR applications and RNase detection and various nucleic acid binding assays.

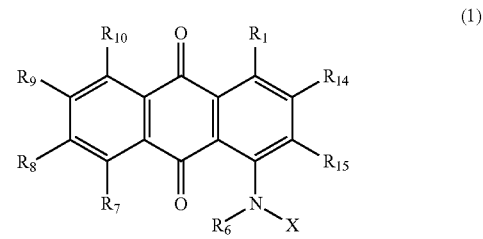

(1)

The compositions of the present invention include anthraquinone compounds of formula (1) wherein the groups $R_7$, $R_8$, $R_9$, and $R_{10}$ can be hydrogen or an electron withdrawing group; the groups $R_1$, $R_{14}$, and $R_{15}$ can be hydrogen or electron donating groups; $R_6$ can be any group other than acetyl that can covalently bind to the nitrogen; X can include a solid support, a biologically relevant molecule, or a linker that can be used to attach the composition to another molecule. In addition, adjacent R groups of $R_{7-15}$ can be part of an aromatic ring or aromatic ring system.

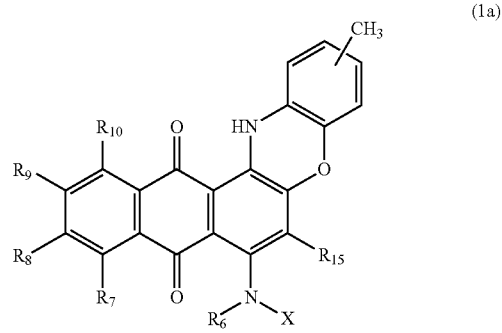

(1a)

Many electron withdrawing groups are known in the art and can be used. Exemplary electron withdrawing groups include nitro, cyano, carboxylate, sulfonyl, sulfamoyl, alkenyl, alkynyl, aryl, heteroaryl, biaryl, bialkenyl, bialkynyl, alkoxycarbonyl, carbamoyl, mono- or di-substituted amino groups, or similar groups that do not substantially diminish quenching. In one embodiment $R_1$ is nitrogen and $R_{14}$ is a heterocyclic group as shown in formula (1a) below.

Many electron donating groups are known in the art and can be used. Exemplary electron donating groups include alkoxy, alkyl, alkylamine, arylamine, cycloalkyl, heteroalkoxy, heteroalkyl, or similar groups that do not substantially diminish quenching.

In formula (1), X can be a biologically relevant molecule and $R_1$ can be $—NR_{16}R_{17}$ wherein $R_{16}$ and $R_{17}$ can independently be hydrogen, alkyl, alkynyl, alkenyl, aryl, heteroaryl, cycloalkyl, heteroalkyl, alkoxy, alkoxycarbonyl, carbonyl, carbamoyl, alkylaryl, heteroalkyl group, or the like. In another embodiment, X includes a biologically relevant molecule and $R_1$ can be $—NR_{16}R_{17}$ wherein one of $R_{16}$ and $R_{17}$ can be hydrogen and the other can be a phenyl or other group.

In one preferred embodiment $R_1$ can be aniline which is bound to the anthraquinone through nitrogen. In another embodiment, $R_1$ is as defined above and $R_6$, $R_7$, $R_8$, $R_9$, or $R_{10}$ are each hydrogen. In another embodiment, of the composition of formula (1), X includes a biologically relevant molecule and $R_1$ is $—NR_{16}R_{17}$ wherein $R_{16}$ and $R_{17}$ can independently be hydrogen, alkyl, alkynyl, alkenyl, aryl, heteroaryl, cycloalkyl, heteroalkyl, alkoxy, alkoxycarbonyl, carbonyl, carbamoyl, alkylaryl, heteroalkyl group, or the like and $R_6$, $R_7$, $R_8$, $R_9$, and $R_{10}$ are each hydrogen. In another embodiment X includes a biologically relevant molecule and $R_1$ is a mono- or di-substituted amine, wherein the substituent is independently, alkyl or aryl, preferably methyl or phenyl; and $R_6$, $R_7$, $R_8$, $R_9$, and $R_{10}$ are each hydrogen.

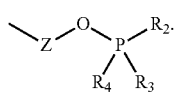

(2)

In certain embodiments X can have the structure of formula (2) wherein the phosphorous in formula 2 can have +3 or +5 oxidation state. In formula (2) Z can be a linking group or a bond and $R_2$, $R_3$, and $R_4$ can be an electron pair, linking group, oxygen, hydrogen, sulfur, alkyl, alkynyl, alkenyl, aryl, heteroaryl, cycloalkyl, heteroalkyl, alkoxy, carbonyl, carbamoyl, alkylaryl, heteroalkoxy, or $—NR_{11}R_{12}$ or $—OR_{13}$, provided that not more than one of $R_{2-4}$ can be an electron pair and that each of $R_{11}$, $R_{12}$, and $R_{13}$ can be either a hydrogen, alkyl, alkynyl, alkenyl, aryl, heteroaryl, cycloalkyl, heteroalkyl, alkoxy, alkoxycarbonyl, carbonyl, carbamoyl, alkylaryl, heteroalkyl group or the like. In one embodiment at least one of $R_{2-4}$ can be a linker that joins the phosphorous to a nucleotide, nucleotide precursor, or nucleotide analog, including a phosphoramidite form of a nucleotide. One preferred embodiment of formula 2 is shown in formula (3).

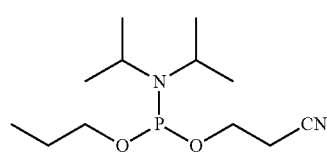

(3)

In certain embodiments of formulas (1) and (1a), X can be the compound of formula (2) and each of $R_2$, $R_6$, $R_7$, $R_8$, $R_9$, and $R_{10}$, can be hydrogen. In another embodiment of formula (1) $R_1$ can be $—NR_{16}R_{17}$ where $R_{16}$ can be hydrogen and $R_{17}$ can be a phenyl or other group; and X can be a compound of formula (3).

In certain embodiments of formulas (1) and (1a), X can be of formula (2) and $R_4$ can be a compound of formula (4), $PG_1$ can be a protecting group as is known in the art or can be a solid support as is known, and $PG_2$ can be any suitable protecting group or can be substituted with a biologically relevant molecule such as a nucleic acid, protein, their precursors or analogs.

In certain embodiments of formulas (1) and (1a), X can be the group of formula (3) and $R_1$ is a mono- or di-substituted amine, wherein the substituent is independently hydrogen, alkyl or aryl, preferably methyl or phenyl; and $R_6$, $R_7$, $R_8$, $R_9$, and $R_{10}$ are each hydrogen. Preferably $R_1$ is a mono- or di-substituted amine wherein one preferred substitution is a phenyl group.

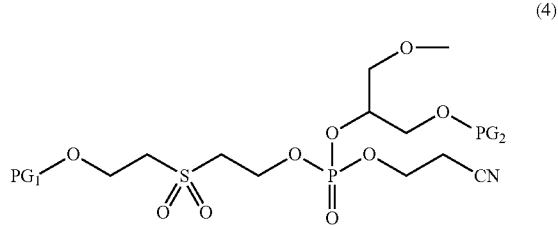

(4)

In certain embodiments of formulas (1) and (1a), X can be a group as in formula (2) wherein $R_4$ includes a nucleic acid or nucleoside or analog thereof that can be attached to the phosphate through a linker.

In certain embodiments of formulas (1) and (1a), X can be a group as in formula (2) wherein $R_4$ includes a nucleic acid or nucleoside or analog thereof that can be attached to the phosphate through a linker and $R_1$ can be a mono or di-substituted amine where the amine substituents can be hydrogen, alkyl, or aryl groups, independently. In one preferred embodiment $R_4$ can be a group as in formula (2) wherein $R_4$ can be formula (4) and $PG_2$ can be a nucleic acid or nucleoside or an analog thereof.

The term "linking group" and "linker" are used interchangeably and refer to a chemical group that is capable of reacting with a "complementary functionality" of a reagent, e.g., to the oxygen of a nucleoside or nucleotide or nucleic acid, and forming a linkage that connects the anthraquinone quenching compound to the reagent. The linking group can be used to link, preferably by way of covalent attachment, an anthraquinone compound to a reagent. When the complementary functionality is amine, preferred linking groups include such groups as isothiocyanate, sulfonylchloride, 4,6-dichlorotriazinyl, carboxylate, succinimidyl ester, other active carboxylate, e.g., $—C(O)halogen$, $—C(O)OC_{1-4}$ alkyl, or $—C(O)OC(O)C_{1-4}$ alkyl, amine, lower alkycarboxy or $—(CH_2)_mN^+(CH_3)_2(CH_2)_mCOOH$, wherein m is an integer ranging from 2 to 12. Typically, when the complementary functionality is amine, the linking group is an N-hydroxysuccinimidyl (NHS) ester. When the complementary functionality is oxygen, the linking group can be of formula (4) wherein $PG_1$ is an oxygen-protecting group or a solid support and $PG_2$ can be the nucleotide. When the complementary functionality is sulfhydryl, the linking group is preferably maleimide, halo acetyl, or iodoacetamide. See R. 35 Haugland (1992) Molecular Probes Handbook of Fluorescent Probes and Research Chemicals, Molecular Probes, Inc., disclosing numerous dyes and modes for conjugating them to a variety of compounds which sections are incorporated herein by reference.

The disclosed anthraquinone quenching compositions can be linked to a variety of molecules and substances without altering their quenching or spectral properties, or in many instances, the biological activity of the reagent. The anthraquinone quenching moiety known as 1-(methylamino)-4-(2-hydroxy-ethylamino)-anthraquinone is abbreviated as UQ1. The anthraquinone quenching moiety known as 1-(phenylamino)-4-(2-hydroxyethylamino)-anthraquinone is abbreviated as UQ2.

The term "protecting group" is symbolized by PG and means a group that is reversibly attached to a moiety that renders that moiety stable in subsequent reaction(s) and that can be selectively cleaved to regenerate that moiety once its protecting purpose has been served. For example, numerous hydroxy-protecting groups are known in the art and can be used. Many such groups are described in Greene, T. W., Protective Groups in Organic Synthesis, 3rd edition 17-237 (1999), which is incorporated herein by reference. Preferably, the hydroxy-protecting group is stable in a basic reaction medium and can be cleaved by acid. Examples of suitable base-stable, acid-labile hydroxy-protecting groups suitable for use with the invention include, ethers, such as methyl, methoxy methyl, methylthiomethyl, methoxyethoxymethyl, bis(2-chloroethoxy)methyl, tetrahydropyranyl, tetrahydrothiopyranyl, tetrahydrofuranyl, tetrahydrothiofuranyl, 1-ethoxyethyl, 1-methyl-1-methoxyethyl, t-butyl, allyl, benzyl, o-nitrobenzyl, triphenylmethyl, .alpha.-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, and triisopropylsilyl; and esters, such as pivaloate, adamantoate, and 2,4,6-trimethylbenzoate. The preferred protecting group for hydroxyl groups, especially the C-5 carbon of a ribose or deoxyribose is the dimethoxytrityl group the use of which is well known in the art.

The present invention also includes methods for making the disclosed compositions. For instance, a compound of formula (1) wherein X is a group as in formula (2) can be prepared by contacting a compound of formula (5) with a compound of formula (6) under conditions suitable for the displacement of the halide ion (HAL). The groups $R_{2-5}$ are as described above, for example, $R_2$ can be an electron pair and $R_3$ and $R_4$ can be diisopropylamino groups. In one method the compound of formula (5) is added to the compound of formula (6) at 0° C. and the reaction mixture is warmed to room temperature with stirring to form the compound of formula (7).

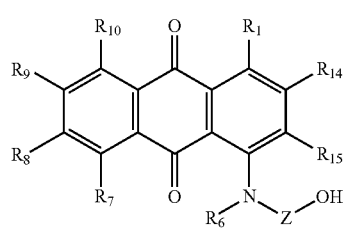

(5)

-continued

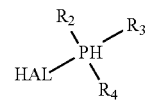

(6)

Where $R_{10}$ is not identical to $R_7$, $R_9$ is not identical to $R_8$, and/or $R_{14}$ is not identical to $R_{15}$ the synthesis will result in isomers which will have nearly identical fluorescent quenching properties.

A linker can then be added to the resulting compound by reacting the product with a compound such as (OH)-L-O-PG under conditions suitable for the addition of —O-L-O-PG at $R_4$. The protecting group (PG) can then be removed such as by reaction with an acid and the linker, L, reacted with a biologically relevant compound, such as a nucleic acid, so that it becomes covalently attached to the anthraquinone through linker, L, as defined above.

Biologically relevant compounds include classes of compounds such as peptides, polypeptides, proteins (e.g., antibodies), nucleic acids (including, e.g., oligonucleotides, nucleosides, whether deoxy or ribonucleotides and their analogs), polysaccharides, and lipids.

The compounds of the invention are identified herein by their chemical structure and/or chemical name. Where a compound is referred to by both a chemical structure and a chemical name, and the chemical structure and chemical name conflict, the chemical structure is determinative of the compound's identity.

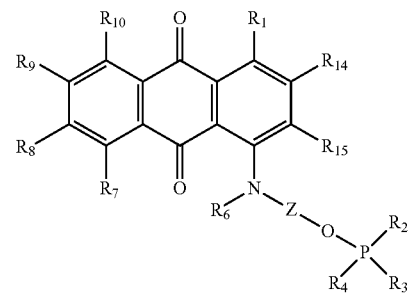

(7)

Another class of reagent encompassed by the invention includes phosphoramidite compounds that incorporate the anthraquinones of formula (1). These compounds are particularly useful for the automated chemical synthesis of nucleic acid polymers with covalently bound anthraquinone compounds of formula (1). Such phosphoramidite reagents, when reacted with nucleophiles such as hydroxyl groups, especially the 5'-hydroxyl group of a nucleoside or nucleotide or nucleic acid, form a phosphite ester linkage that can be oxidized to a phosphate ester linkage by known methods. The phosphoramidite reagents can be nucleosidic or non-nucleosidic.

The invention also provides nucleic acid compositions that contain the disclosed anthraquinone compositions. For example, oligonucleotides containing the disclosed anthraquinone quenchers are contemplated as well as nucleotide precursors for use in the synthesis of such oligonucleotides. Oligonucleotide embodiments can contain regions with internal complementarity. In addition, one or more of the nucleotides can be ribonucleotide(s) or can be analogs of nucleotides.

Methods for preparing anthraquinone-containing oligonucleotides generally involve the use of anthraquinone phosphoramidite precursors or anthraquinone derivatized solid supports that can be used conveniently in conjunction with automated oligonucleotide synthesizers. Such precursors are also contemplated by the present invention. Alternatively, certain oligonucleotides can be prepared such that they have reactive groups that can later be used to join with suitable anthraquinone compositions.

The invention also provides nucleic acid compositions containing, in addition to the a disclosed anthraquinone quencher, a fluorescent dye which emits fluorescence upon exposure to light of the appropriate wavelength. Where the quencher quenches the fluorescence of the fluorophore on the oligonucleotide, suitable dye pairs include at least one of the disclosed anthraquinone quenching compositions and at least one corresponding fluorescent reporter dye that fluoresces within the absorbance spectrum of the quencher such that the fluorescence can be quenched.

In certain embodiments, the dye pair comprises at least one of the disclosed anthraquinone quenching molecules and at least one corresponding fluorescent reporter dye attached to a single compound, such as an oligonucleotide, so that the anthraquinone quencher is within sufficient proximity of the fluorophore to quench its fluorescence. In other embodiments, the fluorescent reporter dye and the anthraquinone quencher can be on different molecules.

Oligonucleotides containing an anthraquinone or dye pair of the invention can be purified by any suitable method. For example, they can be purified by reverse-phase HPLC. Specifically, a sample containing the anthraquinone modified oligonucleotide can be loaded on a reverse-phase column, such as a Hamilton PRP-1 column (1 cm.times.25 cm), and eluted with a linear 5% to 50% acetonitrile gradient over 40 min. The portion of the eluant corresponding to the desired dye-labeled oligonucleotide species can be collected and lyophilized. Because the disclosed anthraquinone quenchers are relatively hydrophobic, this method can be used advantageously in the purification of modified oligonucleotides which will have increased hydrophobicity. The lyophilized oligonucleotide can then be dissolved in water and precipitated, for example with 2% lithium perchlorate in acetone, followed by centrifugation, e.g., at 10,000 g for 10 min. The precipitate can be washed with 10% aqueous acetone.

Oligonucleotides can also be purified by ion-exchange HPLC. For example, the oligonucleotides can be loaded on a 5.times.10 Source™ column (Amersham Pharmacia Biotech, Piscataway, N.J.) and eluted using a linear 0 to 50% gradient of 1 M LiCl in a 0.1 M TRIS buffer having a pH of about 8.0. The portion of the eluant corresponding to the oligonucleotide species can be collected and precipitated with 2% lithium perchlorate in acetone and lyophilized.

A wide variety of reactive fluorescent reporter dyes are known in the literature and can be used so long as they are quenched by the corresponding quencher dye of the invention. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluoroscein, rhodamine or other like compound. Suitable fluorescent reporters include xanthene dyes, such as fluorescein or rhodamine dyes, including 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridin-e and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyl-loxacarbocyanine (CyA); 1H,5H,11H,15H-Xantheno[2,3,4-ij:5,6,7-i'j']diquino-lizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16,17-octahydro-inner salt (TR or TEXAS RED®; BODIPY® dyes; benzoxadiazoles; stilbenes; pyrenes; and the like. The fluorescent emission of certain reporter dyes are provided below.

| Fluorophore | Emission Max |
|---|---|
| Fluorescein | 520 nm |
| Tetrachlorofluorescein (TET) | 536 nm |
| Hexachlorofluorescein (HEX) | 556 nm |
| Cy3 | 570 nm |
| Tetramethylrhodamine (Tamra) | 580 nm |
| Cy3.5 | 596 nm |
| Carboxy-x-rhodamine (Rox) | 605 nm |
| TEXAS RED® | 610 nm |
| Cy5 | 667 nm |
| Cy5.5 | 694 nm |

Many suitable forms of these fluorescent compounds are available and can be used depending on the circumstances. With xanthene compounds, substituents can be attached to xanthene rings for bonding with various reagents, such as for bonding to oligonucleotides. For fluorescein and rhodamine dyes, appropriate linking methodologies for attachment to oligonucleotides have also been described. See for example, Khanna et al. U.S. Pat. No. 4,439,356; Marshall (1975) Histochemical J., 7:299-303; Menchen et al., U.S. Pat. No. 5,188, 934; Menchen et al., European Patent Application No. 87310256.0; and Bergot et al., International Application PCT/U590/05565).

Preferably, when the dye pair is in a configuration in which the reporter dye is effectively quenched by the anthraquinone quencher dye, its fluorescence is reduced by at least a factor of 50%, more preferably by at least 70%, more preferably by at least 80%, 90%, 95%, or 98%, when compared to its fluorescence in the absence of quenching.

Probes having a high signal to noise ratio are desirable for the development of highly sensitive assays. To measure signal to noise ratios relative fluorescence is measured in a configuration where the quencher and fluorophore are within the Forster distance and the fluorophore is maximally quenched (background fluorescence or "noise") and compared with the fluorescence measured when fluorophore and quencher are separated in the absence of quenching ("signal"). The signal to noise ratio of a dye pair of the invention will generally be at least about 2:1 but generally is higher. Signal to noise ratios of about 5:1, 10:1, 20:1, 40:1 and 50:1 are preferred. Ratios of 60:1, 70:1 and even up to 100:1 and higher can also be obtained in some cases. Intermediate signal to noise ratios are also contemplated.

The disclosed anthraquinone quenching compounds effectively quench fluorescence over a surprisingly wide range of wavelengths. For some anthraquinone compositions the absorbance spectrum is in the range of from about 400 to 800 nm, more typically quenching compositions have an absorbance spectrum in the range of about 500 to 700 nm. As indicated previously, the absorbance range of a suitable anthraquinone quencher must overlap the fluorescence emission of the fluorophore of suitable dye pairs. Methods for measuring the effective absorbance range of a quenching composition are known and any suitable method can be used.

Suitable dye-pairs can be used in many configurations. For example, the dye combination can be placed on nucleic acid oligomers and polymers. For example, a dye-pair can be disposed on an oligomer having a hairpin structure such that the fluorophore and quencher are within the Forster distance and FRET occurs. Alternatively, dye pairs can be disposed on an oligomer that can adopt a random coil conformation, such that fluorescence is quenched until the oligonucleotide adopts an extended conformation, as when it becomes part of a duplex nucleic acid polymer. In general, the individual dye moieties can be placed at any position of the nucleic acid depending upon the requirements of use.

Nucleic acid oligomers and polymers that include the dye pairs of the invention can be used to detect target nucleic acids. In one method, the individual components of a dye-pair can be on opposing, annealable, self-complementary segments of an oligonucleotide such that when the oligonucleotide anneals to itself in the absence of exogenous sequences FRET occurs. The oligonucleotide is constructed in such a way that the internal annealing is disrupted and fluorescence can be observed when it hybridizes to nucleic acid polymers having sufficient complementarity. Such an oligonucleotide can be used to rapidly detect nucleic acid polymers having sequences that bind to the oligonucleotide. In another embodiment, such a composition comprises two biomolecules, such as oligonucleotides, one of which is attached to a reporter dye and the other of which is attached as an anthraquinone quencher dye.

Oligonucleotide probes lacking self-complementarity can also be utilized in a similar manner. For example, an anthraquinone quencher and fluorophore can be placed on an oligonucleotide that lacks the self-annealing property such that the random-coil conformation of the oligonucleotide keeps the fluorophore and quencher within a suitable distance for fluorescence quenching. Such oligonucleotides can be designed so that when they anneal to desired target nucleic acid polymers the fluorophore and quencher are more separated and the spectral characteristics of the fluorophore become more apparent.

Other DNA binding formats are also possible. For example, two oligonucleotides can be designed such that they can anneal adjacent to each other on a contiguous length of a nucleic acid polymer. The two probes can be designed such that when they are annealed to such a nucleic acid polymer an anthraquinone quencher on one of the oligonucleotides is within a sufficient proximity to a fluorophore on the other oligonucleotide for FRET to occur. Binding of the oligonucleotides to the nucleic acid polymer can be followed as a decrease in the fluorescence of the fluorophore.

Alternatively, a set of oligonucleotides that anneal to each other such that an anthraquinone quencher and a fluorophore can be positioned on opposing oligonucleotides so that they are within the Forster distance. Incubation of such an oligonucleotide duplex with a nucleic acid polymer that competes for binding of one or both of the oligonucleotides would cause a net separation of the oligonucleotide duplex leading to an increase in the fluorescent signal of the reporter dye. To favor binding to the polymer strands one of the oligonucleotides could be longer or mismatched could be incorporated within the oligonucleotide duplex.

These assay formats can easily be extended to multi-reporter systems where mixtures of distinct oligonucleotides having fluorophores with distinct spectrally resolvable emissions. The binding of individual oligonucleotides can then be detected by determining the fluorescent wavelengths that are emitted from a sample. Such multi-reporter systems are advantageous in applications requiring the analysis of multiple hybridization events in a single reaction volume.

Oligonucleotides can also be configured with the disclosed anthraquinone quenchers such that they can be used to monitor the progress of PCR reactions without manipulating the PCR reaction mixture (i.e., in a closed tube format). The assay utilizes an oligonucleotide that is labeled with a fluorophore and an anthraquinone quencher in a configuration such that fluorescence is substantially quenched. The oligonucleotide is designed to have sufficient complementarity to a region of the amplified nucleic acid so that it will specifically hybridize to the amplified product. The hybridized oligonucleotide is degraded by the exonuclease activity of Taq™ polymerase in the subsequent round of DNA synthesis. The oligonucleotide is designed such that as the oligomer is degraded one of the members of the dye-pair is released and fluorescence from the fluorophore can be observed. An increase in fluorescence intensity of the sample indicates the accumulation of amplified product.

Ribonucleic acid polymers can also be configured with fluorophores and anthraquinone quenchers and used to detect RNase. For example, a dye-pair can be disposed on opposite sides of an RNase cleavage site in an RNase substrate such that the fluorescence of the fluorophore is quenched. Suitable substrates include nucleic acid molecules that have a single-stranded region that can be cleaved and that have at least one internucleotide linkage immediately 3' to an adenosine residue, at least one internucleotide linkage immediately 3' to a cytosine residue, at least one internucleotide linkage immediately 3' to a guanosine residue and at least one internucleotide linkage next to a uridine residue and optionally can lack a deoxyribonuclease-cleavable internucleotide linkage. To conduct the assay the substrate can be incubated with a test sample for a time sufficient for cleavage of the substrate by a ribonuclease enzyme, if present in the sample. The substrate can be a single-stranded nucleic acid molecule containing at least one ribonucleotide residue at an internal position. Upon cleavage of the internal ribonucleotide residue, the fluorescence of the reporter dye, whose emission was quenched by the anthraquinone quencher, becomes detectable. The appearance of fluorescence indicates that a ribonuclease cleavage event has occurred, and, therefore, the sample contains ribonuclease activity. This test can be adapted to quantitate the level of ribonuclease activity by incubating the substrate with control samples containing known amounts of ribonuclease, measuring the signal that is obtained after a suitable length of time, and comparing the signals with the signal obtained in the test sample.

Generally, any of the described assays could be conducted with positive controls that can be used to indicate whether the assay was functioning properly.

The invention also provides kits containing in one or more containers, at least one of the disclosed anthraquinone quenching dye compositions and instructions for its use. Such kits can be useful for practicing the described methods or to provide materials for synthesis of the compositions as described. Additional components can be included in the kit depending on the particular application that utilizes the compounds of the invention. For example, where the kit is directed to measuring the progress of PCR reactions, it may include a DNA polymerase. Where a kit is intended for the practice of the RNase detection assays, RNase-free water could be included. Kits can also contain negative and/or positive controls and buffers.

The following examples further illustrate the invention but, of course, should not be construed as in any way limiting its scope. In particular the following examples demonstrate synthetic methods for obtaining the compounds of the invention. Starting materials useful for preparing the compounds of the invention and intermediates thereof, are commercially available or can be prepared from commercially available materials using known synthetic methods and reagents.

EXAMPLE 1

This example demonstrates the conversion of 1,4-hydroxyl groups of an anthraquinone compound 1 to leaving groups as shown in Scheme 1. "E" in compound 2 can be any suitable leaving group. Many suitable leaving groups are known in the art and can be used, for example, halides, aryl alkylsulfonyloxy, substituted arylsulfonyloxy (e.g., tosyloxy or mesyloxy), substituted alkylsulfonyloxy (e.g., haloalkylsulfonyloxy), phenoxy or substituted phenoxy, and acyloxy groups. Compounds of type 1 are available commercially (e.g., Aldrich Chemical Co., Milwaukee, Wis.). The reaction requires a suitable base which includes bases having a pKa of about 10 or more. Suitable bases include alkylamine bases like triethylamine, dipropylamine; metal amide bases, including lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; hydride bases including sodium hydride and potassium hydride. Alkylamine bases, like triethylamine are preferred.

To convert compound 1 to compound 2, a solution of about 1 to about 1.2 equivalents of a suitable base is added to a stirred solution of compound 1 in a suitable organic solvent under an inert atmosphere, such as argon. Suitable organics solvents include moderately polar aprotic solvents. The solution is maintained at a constant temperature between about −100° C. or higher to about room temperature, and more preferably between about −80° C. to about 20° C. The base is diluted in a suitable organic solvent before the addition and is added slowly enough to avoid over heating the reaction. Organic solvents suitable for the conversion of compound 1 to compound 2 include those solvents in which the reactants and products are soluble and include dichloromethane, diethyl ether, tetrahydrofuran, benzene, toluene, xylene, hydrocarbon solvents (e.g., pentane, hexane, and heptane), and mixtures thereof. After addition of the base, the reaction mixture is stirred for about 1 to 4 h such that the reaction-mixture temperature remains within several degrees of the starting temperature. The temperature can then be adjusted to between about −20° C. to about room temperature, preferably to about room temperature, and the reaction stirred until it is substantially complete as determined analytically, as by thin-layer chromatography or high-performance liquid chromatography. Then the reaction mixture can be quenched and compound 2 isolated by standard methods.

EXAMPLE 2

This example demonstrates the conversion of the 1,4-leaving groups of compound 2 to 1-substituted amino-4-β-hydroethylaminoanthraquinones 4 according to Scheme 2.

A solution of about 1 equivalent of compound 2 is dissolved in a suitable organic solvent under an inert atmosphere. Suitable solvents include polar aprotic solvents such as, dimethylformamide, acetonitrile, and dimethylsulfoxide in which compound 2 is soluble. The solution is maintained at room temperature during the addition of about 10 equivalents of the substituted amine and stirred for about 1 h to 4 h at a temperature of about 150° C. until the reaction is substantially complete as determined analytically by thin-layer chromatography or high-performance liquid chromatography. The reaction mixture is then cooled to room temperature and quenched to give compounds 3 and 3'. Compounds 3 and 3'

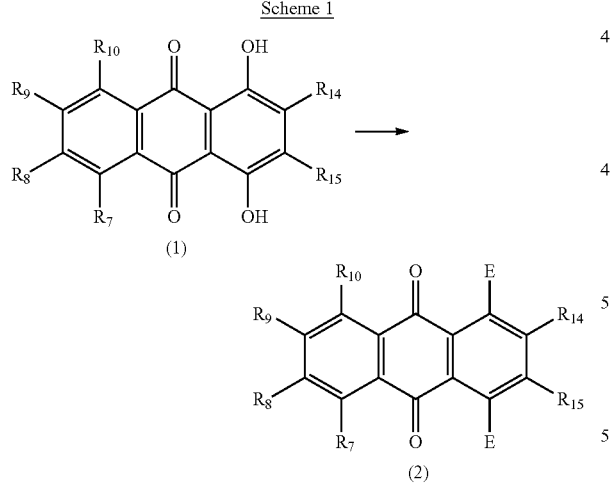

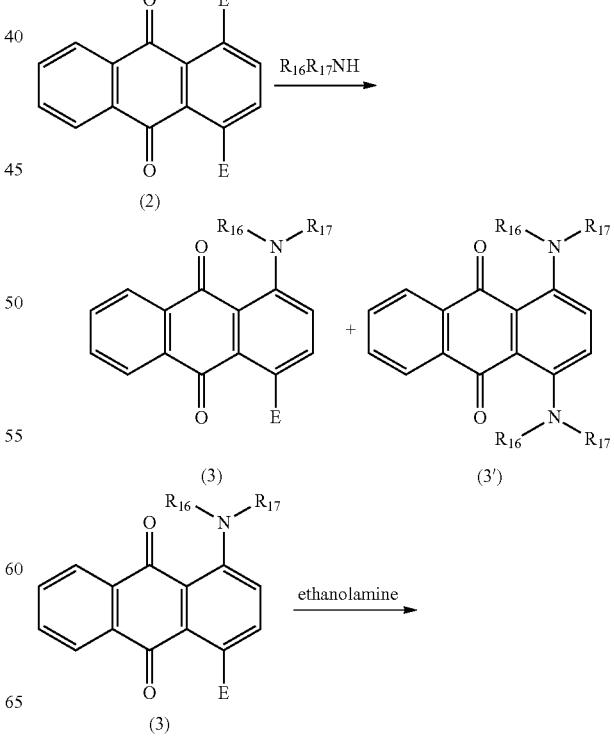

15

-continued

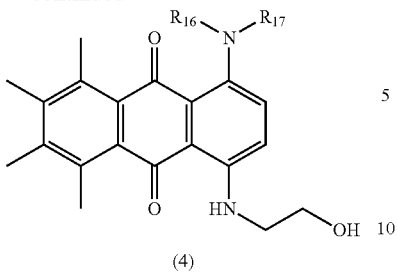

(4)

can be separated by flash chromatography or HPLC to obtain compound 3. Alternatively, compounds 3 and 3' 9 can be treated with ethanolamine to prepare compound 4 prior to separation.

To obtain compound 4 a solution of about 1 equivalent of compound 3 is dissolved in a suitable organic solvent, as defined previously in this example, under an inert atmosphere. About 250 equivalents of ethanolamine is added in a single addition and the reaction mixture is stirred for about 1 to about 3 h, preferably 2 h at about 100° C. until the reaction is substantially complete as determined analytically by thin-layer chromatography or high-performance liquid chromatography. The reaction mixture is then cooled to room temperature and quenched to give compound 4 which can be purified further by a variety of well known techniques, including preparatory high-performance chromatography or flash chromatography.

EXAMPLE 3

This example demonstrates synthesis of 1-substituted amino-4-(2-cyanoethyl-phosphoramidite-ethylamino)-anthraquinone as shown in Scheme 3. A 2 M solution of anthraquinone 4 in triethylamine is prepared. The solution is cooled to about 0° C. and about 1-2 equivalents of a phosphonic chloride compound is added. The reaction mixture is warmed to room temperature and allowed to stir for about 4 h until the reaction is substantially complete as

16

-continued

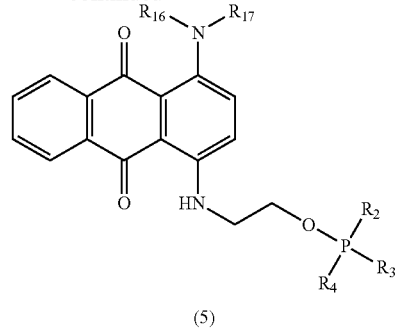

(5)

determined analytically. The reaction mixture is quenched and compound 5 is isolated by standard procedures.

The method can be used to synthesize anthraquinone phosphoramidite compounds wherein each occurrence of $R_{16}$, $R_{17}$, and $R_{7-10}$ is independently hydrogen, alkyl, alkynyl, alkenyl, aryl, heteroaryl, cycloalkyl, heteroalkyl, alkoxy, alkoxycarbonyl, carbonyl, carbamoyl, alkylaryl, heteroalkyl group, or the like. $R_{2-6}$ are independently an electron pair, oxygen, hydrogen, alkyl, alkenyl, alkynyl, aryl, heteroaryl, cycloalkyl, heteroalkyl, alkoxy, alkoxycarbonyl, carbamoyl, or similar substituent, or a mono- or di-substituted amine as defined previously; and HAL represents a halogen atom, typically chlorine.

EXAMPLE 4

This example demonstrates synthesis of an anthraquinone quencher covalently linked to a linker (L) as shown in Scheme 4. Anthraquinone compound 5 is mixed for about 0.5 h under an inert atmosphere with a hydroxy-containing linker compound (HO-L) and ethylthiotetrazole in a suitable organic solvent as in Example 2. L could be a nucleotide or nucleic acid polymer. A second solution of compound 5 in acetonitrile and ethylthiotetrazole is then added and the reaction mixture stirred for an additional 0.5 h. The reaction mixture is washed with acetonitrile and treated with 10% (v/v) methylimidazole in THF/pyridine (8:1) under an inert atmosphere for about 0.5 h. The reaction product is separated and washed with acetonitrile and treated with 0.02 M iodine in THF/pyridine/H$_2$O (78:20:2), which is added slowly over 5 min. The reaction mixture is isolated and dried overnight in a vacuum to provide compound 6. L could be a nucleotide or oligonucleotide with a free hydroxyl group.

Scheme 3

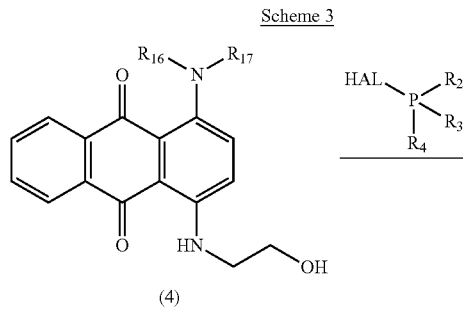

Scheme 4

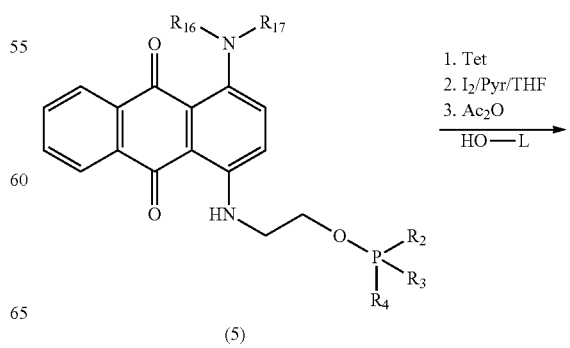

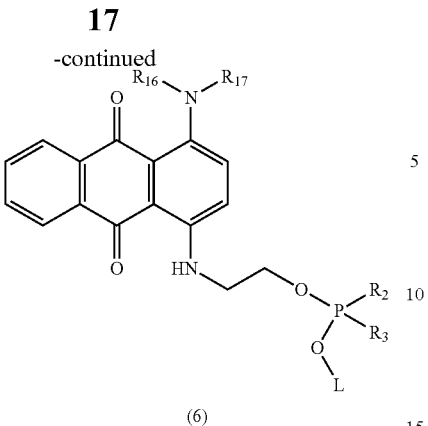

(6)

EXAMPLE 5

This example demonstrates the conversion of a single hydroxyl group of an anthraquinone to a leaving group as shown in Scheme 6. Suitable leaving groups are as defined above in Example 1.

To convert a compound 8 to compound 9, a solution of about 1 to about 1.2 equivalents of a suitable base is added to a stirred solution of a monohydroxy-anthraquinone 8 in an organic solvent under an inert atmosphere. The solution is maintained at a constant temperature between about −100° C. to about room temperature, and more preferably between at about −80° C. to about 20° C. The base is diluted in a suitable organic solvent, as described in Example 2, before the addition and is added to avoid over heating of the reaction mixture. After addition of the base, the reaction mixture is allowed to stir for about 1 to 4 h such that the temperature remains within several degrees of the starting temperature. The temperature can then be adjusted to between about −20° C. to about room temperature, preferably to about room temperature, and the reaction stirred until it is substantially complete as determined analytically, such as by thin-layer chromatography or high-performance liquid chromatography. The reaction mixture is quenched and compound 9 is isolated by standard methods.

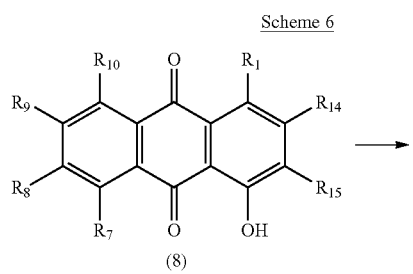

EXAMPLE 6

This example demonstrates a method useful for converting the leaving group of anthraquinone compound 9 to the corresponding amino-4-β-hydroxyethylaminoanthraquinone 10 as shown in scheme 7.

A solution of about 1 equivalent of compound 9 is dissolved in a suitable organic

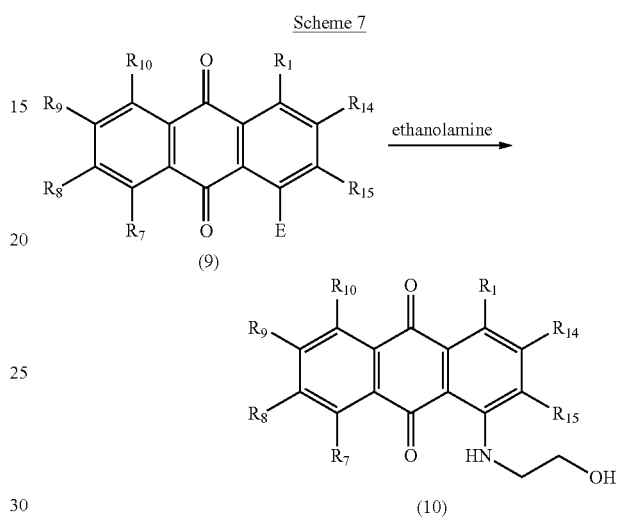

solvent, as described above, under an inert atmosphere. About 250 equivalents of ethanolamine is added to this solution in a single aliquot. The reaction mixture is allowed to stir for about 1 to about 3 h, depending on the rate of stirring, preferably 2 hours at about 100° C. with stirring at a rate that maintains the temperature at about 100° C. Stirring is continued until the reaction is substantially complete as determined analytically, such as by thin-layer chromatography or high-performance liquid chromatography. The reaction mixture is then cooled to room temperature and quenched to provide compound 10 which can be purified by known techniques such as, preparative HPLC or flash chromatography.

EXAMPLE 7

This example demonstrates the synthesis of 1-substituted amino-4(2-cyanoethyl phosphoramidite-ethylamino)-anthraquinone as shown in scheme 8. A 2 M solution of anthraquinone compound 10 is prepared in triethylamine. The solution is cooled to 0° C. and

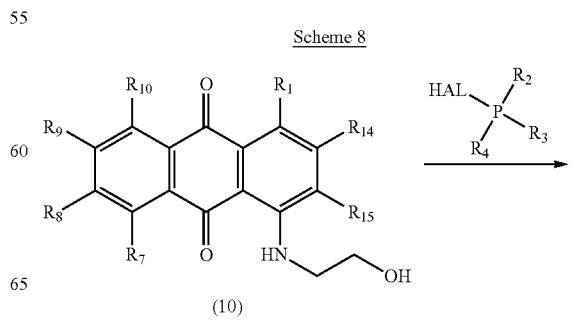

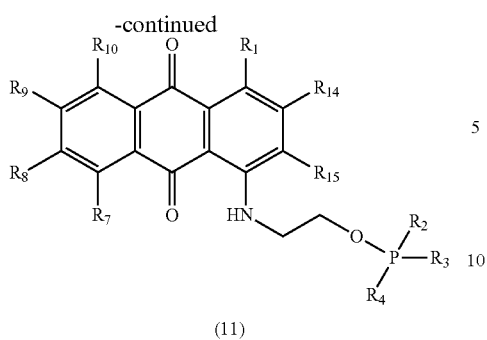

(11)

about 1-2 equivalents of a phosphonic chloride compound is added. The reaction mixture is warmed to room temperature and stirred for about 4 h until substantially complete as determined analytically. The reaction mixture is quenched and compound 11 is isolated by standard methods.

EXAMPLE 8

This example demonstrates the synthesis of an anthraquinone quencher that is covalently bonded to a linker (L) as shown in Scheme 9. Anthraquinone compound 11 is dissolved in an organic solvent, such as acetonitrile, with ethylthiotetrazole and HO-L under an inert atmosphere. L could be a nucleotide or nucleic acid polymer. The solution is maintained at room temperature and stirred for about 0.5 h. A second solution of 11 in acetonitrile and ethylthiotetrazole is added to the reaction mixture with stirring for an additional 0.5 h. The reaction mixture is washed with acetonitrile and treated with 10% (v/v) acetic anhydride solution in THF and mixed with an equal volume of 10% (v/v) methylimidazole in an 8:1 mixture of

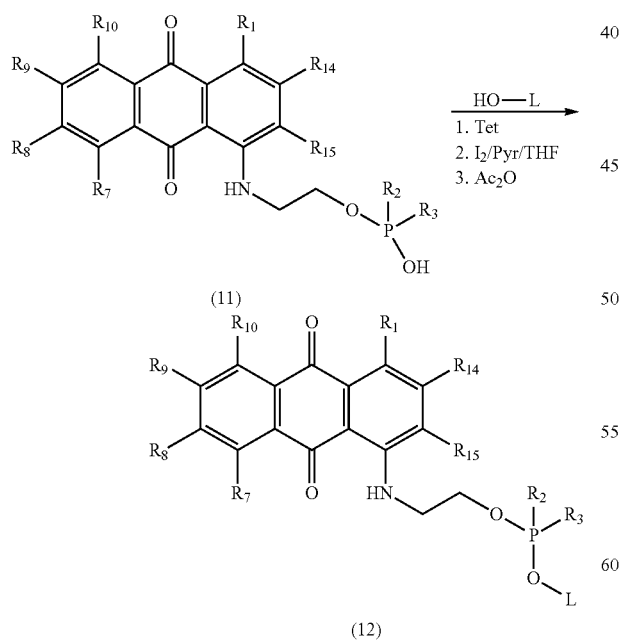

THF/pyridine, all under an inert atmosphere. After about 30 min the reaction mixture is washed with acetonitrile and treated with 0.02 M iodine in THF/pyridine/H$_2$O solution (78:20:2), which is added over 5 min. The reaction mixture is isolated and dried overnight under vacuum to obtain compound 12.

EXAMPLE 9

This example demonstrates the synthesis of 1-(methylamino)-4-(2-cyanoethylphosphoramidite-ethylamino)-anthraquinone 14 as shown below.

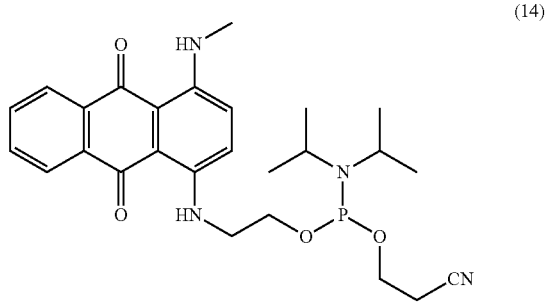

(14)

N,N-diisopropylaminocyanoethyl-phosphonamidic chloride (0.10 mL, 0.51 mmol) was added dropwise at 0° C. to a solution of 1-(methylamino)-4-(2-hydroxy-ethylamino)-anthraquinone (100 mg, 0.34 mmol) and triethylamine (TEA) (0.12 mL, 0.68 mmol). The mixture was stirred at room temperature for 4 h. The solvent was removed and the residue was dissolved in ethylacetate (EtOAc) (2 mL). The product was isolated by flash chromatography on silica with EtOAc/petroleum ether (PE)/TEA: 40/50/10). .sup.1H NMR (CDCl$_3$) .delta.10.83 (t, J=5 Hz, 1H), 10.57 (d, J=5 Hz, 1H), 8.29-8.34 (m, 2H), 7.65-7.70 (m, 2H), 7.28 (d, J=10, 1H), 7.20 (d, J=10, 1H), 3.90-4.00 (m, 2H), 3.80-3.90 (m, 2H), 3.58-3.67 (m, 4H), 3.08 (d, J=5, 3H), 2.65 (t, J=6, 2H), 1.18 Ct J=6, 12H). MS (FAB') [M+]: calculated for C$_{26}$H$_{33}$N$_4$O$_4$P, m/z 496.54; found, m/z 512.

EXAMPLE 10

This example demonstrates the synthesis of 1-(phenylamino)-4-(2-hydroxyethylamino)-anthraquinone 15 as shown below. Aniline (49.8 mL, 547 mmol) was added to 1,4-bis(tosyloxy)anthraquinone (See Zielake, J. Org. Chem. 52: 1305-1309 (1987) (3 g, 5.47 mmol) in DMSO (120 mL) and heated at 150° C. for 2 h. The reaction was allowed to cool to

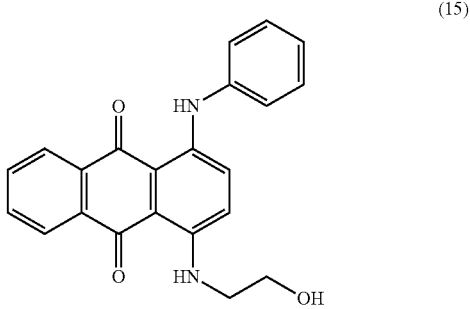

(15)

room temperature and poured into 15% HCl solution (1.5 L), filtered and rinsed with water to give a reddish solid. The solid consisted of 1-(phenylamino)-4-(tosyloxy)anthraquinone (red color on TLC, Rf 0.65, 20% EtOAc/PE) and 1,4-bis-(phenylamino)anthraquinone (blue color on TLC, Rf 0.75, 20% EtOAc/PE). The solid was dried overnight under vacuum to give 2.2 g of a reddish solid. Ethanolamine (72 mL, 1173 mmol) was added to the reddish solid (2.2 g, 4.69 mmol) in DMSO (30 mL). The mixture was heated at 100° C. for 2 h. The reaction was brought to room temperature, poured into 10% HCl (1.5 L) and extracted with $CH_2Cl_2$ (3.times.). The organic layer was washed with water (1.times.), dried over sodium sulfate and evaporated. Flash chromatography on silica with 50-100% EtOAc/PE gave a blue solid (0.6 g, 42% yield). TLC: Rf 0.45, 30% EtOAc/PE. .sup.1H NMR ($CDCl_3$) .delta.12.09 (s, 1H), 10.81 (s, 1H), 8.26-8.32 (m, 2H), 7.74-7.76 (m, 1H), 7.67-7.71 (m, 2H), 7.52 (d, J=10 Hz, 1H), 7.37-7.42 (m, 2H), 7.31 (d, J=8 Hz, 1H), 7.24-7.26 (m, 1H), 7.13-7.19 (m, 2H), 3.96 (t, J=5 Hz, 2H), 3.59 (q, J=5 Hz, 2H). MS (FAB') [M+]: calculated for $C_{22}H_{18}N_2O_3$, m/z 358.39; found, m/z 358.

EXAMPLE 11

This example demonstrates the synthesis of 1-(phenylamino)-4-(2-cyanoethylphosphoramidite-ethylamino)-anthraquinone 16 as shown below.

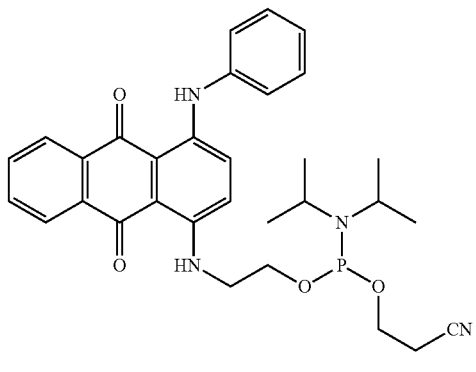

(16)

N,N-diisopropylamino-cyanoethylphosphonamidic chloride (0.93 mL, 4.19 mmol) was added dropwise to a solution of 1-(phenylamino)-4-(2-hydroxy-ethylamino)-anthraquinone (1 g, 2.79 mmol) and TEA (0.8 mL, 5.58 mmol) at 0° C. The mixture was stirred at room temperature for 3 h. The solvent was removed and the residue was dissolved into EtOAc (3 mL). Flash chromatography on silica with EtOAc/PE/TEA: 5/85/10-50/40/10 gave a blue solid (1.28 g, 82% yield). TLC: Rf 0.70, EtOAc/PE/TEA: 40/50/10).sup.1H NMR ($CDCl_3$) .delta.12.16 (s, 1H), 10.88 (t, J=5 Hz, 1H), 8.34 (dt, J=7,2,2 Hz, 2H), 7.69-7.75 (m, 2H), 7.60 (d, J=10 Hz, 1H), 7.39 (t, J=7 Hz, 2H), 7.26 (t, J=4 Hz, 2H), 7.15-7.20 (m, 2H), 3.92-4.00 (m, 2H), 3.82-3.90 (m, 2H), 3.60-3.69 (m, 4H), 2.67 (t, J=6 Hz, 2H), 1.19 (t, J=7 Hz, 12H). MS (FAB') [M+]: calculated for $C_{31}H_{35}N_4O_4P$. m/z 558.61; found, m/z 558.

EXAMPLE 12

This example demonstrates the synthesis of 1-(phenylamino)-4-(2-hydroxyethylamino)-anthraquinone-DMT-CPG 17, 19 also known as UQ2, as shown.

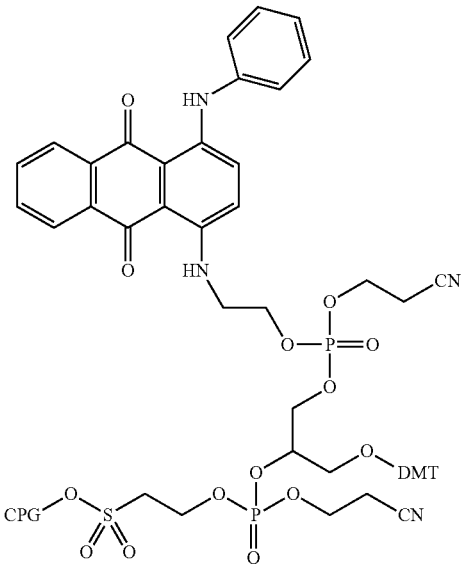

(17)

Two grams of derivatized controlled porous glass (CPG) support 18 were treated with 10 mL of 3% (v/v) dichloroacetic acid in dichloromethane three separate times and washed with 5.times.10 ml of acetonitrile to provide compound 18.

A solution of 0.5 g of mono DMT-glycerol phosphoramidite (17a) in 5 mL of

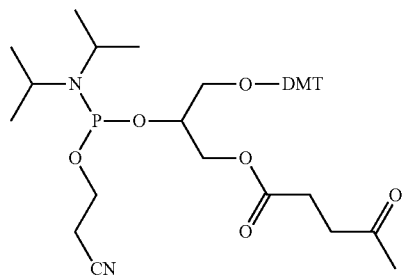

(17a)

dry acetonitrile and 5 mL of 0.45 M ethylthiotetrazole was added to 18 under an argon atmosphere. After 20 min the reaction mixture was isolated, and the CPG washed with 5×10 mL

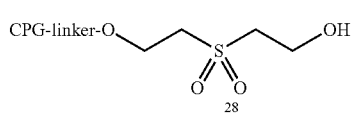

(18)

of acetonitrile, followed by 10 mL of 10% (v/v) acetic anhydride solution in THF with 10 mL of a solution containing 10% (v/v) methylimidazole in 8:1 THF/pyridine, all under argon. After 30 min the reaction mixture was removed and the derivatized CPG was washed with 5.times.10 mL of acetonitrile, followed by 10 mL of 0.02 M iodine in THF/pyridine/$H_2O$ (78:20:2) solution, which was allowed to react with the CPG for 5 min. The treated CPG was isolated and washed with 5.times.10 mL of acetonitrile. A solution of 0.5 M hydrazine hydrate in 1:8 acetic acid/pyridine was mixed with the CPG under an argon atmosphere and the mixture allowed to react for 30 min. The CPG material was then isolated and washed with 5.times.10 mL of acetonitrile. A solution of 0.3 g of phosphoramidite 16 in 5 mL of dry acetonitrile and 5 mL of 0.45 M ethylthiotetrazole was added to the resulting CPG under an argon atmosphere. After 20 min the reaction mixture was removed and a fresh solution of 0.3 g of phosphoramidite 16 in 5 mL of dry acetonitrile and 5 mL of 0.45 M ethylthiotetrazole was added to resulting CPG under argon and allowed to react for an additional 20 min. (72 mL, 1173 mmol) The reaction mixture was removed, and CPG was washed with 5.times.10 mL of acetonitrile. A 10 mL solution of 10% (v/v) acetic anhydride solution in THF and 10 mL of 10% (v/v) methylimidazole in 8:1 mixture of THF/pyridine were added to resulting CPG under argon. After 30 min the reaction mixture was removed and CPG was washed with 5.times.10 mL of acetonitrile. The phosphite was oxidized to the phosphate by treatment with 10 mL of 0.02 M iodine in THF/pyridine/H$_2$O (78:20:2) for 5 min. The reaction mixture was removed and the derivatized CPG washed with 5.times.10 mL of acetonitrile, followed by 2.times.10 mL of dichloromethane and dried overnight under vacuum to provide 2.2 g of derivatized CPG product.

EXAMPLE 13

This example demonstrates a method for the synthesis of bis-1,4-(4-hydroxyethylphenylamino)-anthraquinone (19) according to the invention.

The starting material 4-phenethylamino alcohol (1.25 g, 9.1 mmol) was mixed with 1,4-Bis(tosyloxy)anthraquinone (0.5 g, 0.91 mmol) in DMSO (2 mL) and the mixture was heated at 180° C. for 16 h. Then 1M HCl solution was mixed in and the reaction was filtered and rinsed with water to give a blue solid. The solid was dried under vacuum and redissolved in ethylacetate (3 mL) with heat to facilitate dissolution. Purification of the product by flash chromatography in ethylacetate gave two solid compounds, one of which was blue the other of which was green. NMR analysis was used to confirm that the green compound was the desired product (0.19 g). .sup.1H NMR (CDCl$_3$).delta.12.23 (s, 1H), 8.36-8.40 (m, 2H), 7.73-7.77 (m, 2H), 7.48 (s, 2H), 7.21-7.27 (m. 9H), 3.89 (t, J=7 Hz, 4H), 2.89 (t, J=7 Hz, 4H), 1.48 (bs, 3H).

The above reaction was repeated in a larger scale using identical but scaled up conditions (ie. 15 g of 1,4-Bis(tosyloxy)-anthraquinone, 18.75 g (5 eq) of 4-phenethylamino alcohol in 30 mL DMSO). Half of the crude solid was purified using flash chromatography to provide 1 g of bis-1,4-(4-hydroxyethyl-phenylamino)-anthraquinone.

These results demonstrate a method for preparing bis-1,4-(4-hydroxyethylphenylamino)-anthraquinone that is scalable.

EXAMPLE 14

This example demonstrates a method for the synthesis of 1-(4-hydroxyethylphenylamino)-4-(DMT-4-hydroxyethylphenylamino)-anthraquinone (20) according to the invention. Dissolved dimethoxytrityl chloride (DMTCl) (0.3 g, 0.89 mmol) in anhydrous pyridine (15 mL) was added dropwise into a solution of bis-1,4-(4-hydroxyethyl-phenylamino)-anthraquinone in pyridine (15 mL) and allowed to react overnight. Analysis of the reaction products by thin layer chromatography showed two new products.

Pyridine was removed from the reaction mixture under a vacuum and the product was purified by flash chromatography with ethylacetate to provide two products having R$_f$ values of 0.5 and 0.8 along with starting material. .sup.1H NMR was used to confirm that the compound having an R$_f$ of 0.5 in ethylacetate was the desired product. .sup.1H NMR (CDCL$_3$) .delta.12.28 (s, 1H), 8.40-8.44 (m, 2H), 7.77-7.81 (m, 2H), 7.50 (s, 2H), 7.40-7.42 (m, 2H), 7.20-7.33 (m, 18H), 6.81-6.88 (m, 4H), 3.92 (t, J=6 Hz, 2H), 3.81 (s, 6H), 3.33 (t, J=7 Hz, 2H), 2.92 (t, J=7 Hz, 4H).

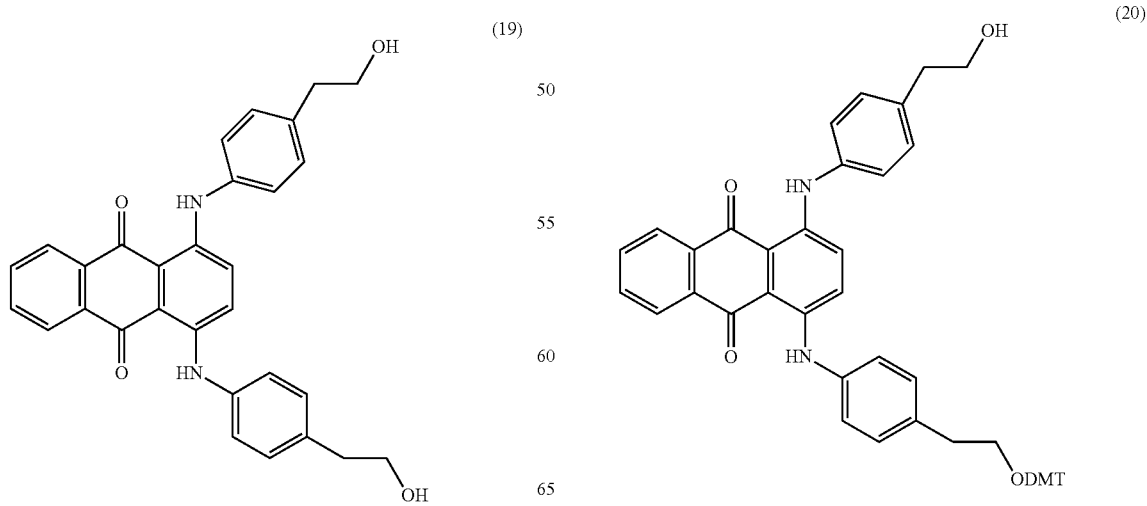

EXAMPLE 15

This example demonstrates the synthesis of 1-(β-cyanoethylphosphoramidite-4-hydroxyethyl-phenylamino)-4-(DMT-4-hydroxyethyl-phenylamino)-anthraquinone (21)

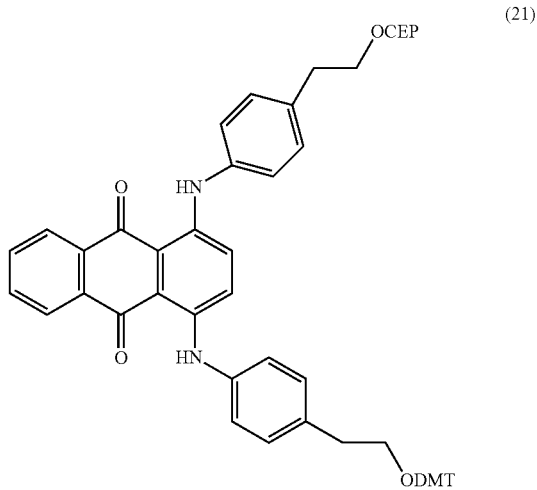

(21)

according to the invention.

β-cyanoethyl N,N,N',N'-tetraisopropylphosphorodiamidite (0.81 mL, 1.79 mmol) and 0.5 eq diisopropylamine 1H-tetrazole (60 mg, 0.64 mmol) were mixed into a solution of 1-(4-hydroxyethyl-phenylamino)-4-(DMT-4-hydroxyethyl-phenylamino)-anthraquinone (0.53 g, 1.28 mmol) in THF (10 ml). After 12 h the solid material was removed by filtration and the solvent was removed under a vacuum. The remaining oil residue was dissolved in a solvent that contained ethylacetate/petroleum ether/triethylamine (40/45/5) and loaded onto a silica column for flash chromatography in ethylacetate/petroleum ether/triethylamine: 20/75/5-40/45/5) to provide a blue oil (0.32 g, 26% yield) which has an $R_f$ of 0.75 in a silica thin layer chromatography plate developed with ethylacetate/petroleum ether/triethylamine 40/45/5).

EXAMPLE 16

This example demonstrates the synthesis of oligonucleotides comprising an anthraquinone quencher dye and the measurement of the absorbance spectra of several anthraquinone quenchers.

An oligonucleotide bearing the anthraquinone quencher (UQ2) of the class of the invention was synthesized; its absorbance spectra was characterized and compared to the absorbance spectra of other representative dark quenchers, dabcyl, and QSY7.

The following oligonucleotides were synthesized:

```
SEQ ID No 1:      CAGAGTACCTGA-UQ2

SEQ ID No 2:      CAGAGTACCTGA-QSY7

SEQ ID No 3:      CAGAGTACCTGA-Dabcyl
```

For all sequences A, C, G, T represent deoxynucleotides (DNA) and the oligonucleotide sequences are written with the 5' end to the left and the 3' end to the right unless otherwise noted. Oligonucleotide substrates were synthesized with the anthraquinone quencher UQ2, QSY7, and Dabcyl using standard phosphoramidite chemistry on an Applied Biosystems Model 394 DNA/RNA synthesizer. For the synthesis of SEQ ID NO 1 and all oligonucleotides containing UQ2, the CPG bound anthraquinone precursor prepared in Example 12 was used unless otherwise noted. The synthesis were carried out on a 1 .mu.mole scale. Thus, UQ2 derivatized solid support starting material contained 1 .mu.mole of reactive sites on the support were placed into a synthesis chamber and phosphoramidite nucleotides were added by standard chemical methods.

Following synthesis, the solid support was transferred to a 2 ml microcentrifuge tube where oligonucleotides were cleaved from the solid support by standard methods.

Oligonucleotides were purified by reverse-phase HPLC with a Hamilton PRP-1 column (1.0 cm.times.25 cm) using a linear gradient of from 5 to 50% acetonitrile over 40 min in 0.1 M triethyl-ammonium acetate (TEAAc) at pH 7.2. Samples were monitored at 260 nm and 494 nm and peaks corresponding to the fluorescent-labeled oligonucleotide species were collected, pooled, and lyophilized.

Oligonucleotide samples were dissolved in 200 mu.l of sterile water and precipitated by adding 1 ml of 2% LiClO$_4$, followed by centrifugation at 10,000 g for 10 min. The supernatant was decanted and the pellet washed with 10% aqueous acetone.

Oligonucleotides were repurified by ion exchange HPLC using a 40 min linear gradient of 0% to 50% 1 M LiCl in 0.1 M TRIS buffer. Samples were monitored at 260 nm and 494 nm and peaks corresponding to the dual-labeled oligonucleotide species were collected, pooled, precipitated with 2% LiClO$_4$, and lyophilized.

Compound identities were verified by mass spectroscopy using a Voyager-DE BioSpectrometry workstation by known methods.

The oligonucleotides were suspended in HPLC grade water at 400 nM concentration. The absorbance spectra were measured in 10 mM Tris pH 8.0, 1 mM EDTA (TE buffer) with a sub-micro quartz cuvette having a 1-cm path length in a Hewlett Packard Model 8453 spectrophotometer (Hewlett Packard, Palo Alto, Calif.). Optical absorbance density was recorded from 200 to 750 nm for each oligonucleotide. Individual absorbance spectra are shown in FIG. 1.

The data in this example shows that the anthraquinone (UQ2) absorption spectrum is broad, ranging from about 500 to about 700 nm. This absorbance range overlaps the fluorescence emission range of many fluorophores commonly used in molecular biology applications. UQ2 can be used to quench the fluorescence of at least the following dyes: fluorescein, tetrachlorofluoroscein, hexachlorofluoroscein, Cy3, tetramethylrhodamine, Cy3.5, carboxy-x-rhodamine, TEXAS RED®, Cy5, Cy5.5.

EXAMPLE 17

This example demonstrates the use of anthraquinone-quenched fluorescent probes to detect PCR amplified DNA.

Fluorescence-quenched probes can be employed to detect amplified target nucleic acid sequence during a PCR reaction. In this assay, a fluorescence-quenched probe that anneals to the 3' side of an amplification primer is degraded by the nuclease activity of Taq DNA polymerase during a round of polymerization. Fluorescence can then be detected during the PCR reaction as the probe is degraded and the quencher and fluorophore are separated.

Oligonucleotide primers and probes were synthesized as in Example 16 with the exception that with Cy5 containing probes, deprotection was with 1:1:2 t-BuNH$_2$:MeOH:H$_2$O and samples were incubated for 4 h at 65° C. The supernatant was removed and the CPG was washed with 1 ml of H₂O and supernatants were pooled and dried. Fluorophores were added to the 5' nucleotide by standard methods. Primers, probes, and target nucleic acids are shown in Table 1 below. Probes used are SEQ ID No. 4, 5, 6, 7, and 8. Primers used are SEQ ID No. 9 and 10. The target nucleic acid is SEQ ID No. 11, a 220 basepair (bp) amplicon derived from the murine bHLH protein Ptfl-p48 gene (Genbank #AF298116), cloned into the pCRII-TOPO vector (Invitrogen, Carlsbad, Calif.), and is hereafter referred to as the "p48-gene target".

TABLE 1

Probes:

| | |
|---|---|
| 6FAM-ACCCGTTCACCCTCCCCCAG-UQ2 | SEQ ID No. 4 |
| 6FAM-ACCCGTTCACCCTCCCCCAG-6Tamra | SEQ ID No. 5 |
| 6FAM-ACCCGTCACCCTCCCCCAG-QSY7 | SEQ ID No. 6 |
| TR-ACCCGTTCACCCTCCCCCAG-UQ2 | SEQ ID No. 7 |
| Cy5-ACCCGTFfCACCCTCCCCCAG-UQ2 | SEQ ID No. 8 |

Forward Primer: MP48 F968

| | |
|---|---|
| CAGAAGGTTATATCTGCCATCG | SEQ ID No. 9 |

Reverse Primer: MP48 R1187

| | |
|---|---|
| CTCAAAGGGTGGTTCGTTCTCT | SEQ ID No. 10 |

Target Amplicon (SEQ ID No. 11)
Forward Primer F968      Probe
CAGAAGGTTTATCATCTGCCATCGAGGCACCCGTTCACCCTCCCCCAG
TGACCCGGATTATGGTCTCCCTCCTCTTGCAGGGCACTCTCTTTCCTG
GACTGATGAAAAACAGCTCAAAGAACAAAATATCATCCGTACAGCTAA
AGTGTGGACCCCAGAGGACCCCAGAAAACTCAACAGTCAAATCTTTCG
ACAACATAGAGAACGAACCACCCTTTGAG
         Reverse Primer R1187

PCR amplification was done using the Stratagene (La Jolla, Calif.) Brilliant Plus Quantitative PCR core Reagent Kit according to the manufacturer's directions. Reactions were carried out in a 25 mu.L volume and comprised 200 nM each of the amplification primers and fluorescent quenched probe and about 1000 copies of the target DNA. Cycling conditions were 50° C. for 2 min, 95° C. for 10 min, then 40 cycles of 2-step PCR with 95° C. for 15 sec and 60° C. for 1 min. PCR and fluorescence measurements were done using an ABI Prism™ 7700 Sequence Detector (Applied Biosystems Inc., Foster City, Calif.). All data points were performed in triplicate. Results for different probes are presented in Table 2 below. The cycle threshold (Ct) value is defined as the cycle at which a statistically significant increase in fluorescence is detected above background. Typically, a lower Ct value is indicative of a higher concentration of target DNA. However, in this example, where the amount of target DNA is held constant the Ct value of a given oligonucleotide is indicative of probe sensitivity. The assays were performed using an identical amount of input target DNA (1.times.10.sup.3 copies of the p48-gene target plasmid). Table 2 shows that all oligonucleotides provided similar Ct values and therefore function similarly.

TABLE 2

Ct values for PCR Assays

| Probe | Reporter-Quencher | Avg. Ct Value |
|---|---|---|
| SEQ ID No. 4 | 6FAM-ACCCGTTCACCCTCCCCCAG-UQ2 | 27.64 |
| SEQ ID No. 5 | 6FAM-ACCCGTTCACCCTCCCCCAG-6Tamra | 27.67 |
| SEQ ID No. 6 | 6FAM-ACCCGTTCACCCTCCCCCAG-QSY7 | 28.01 |

Figure 2:
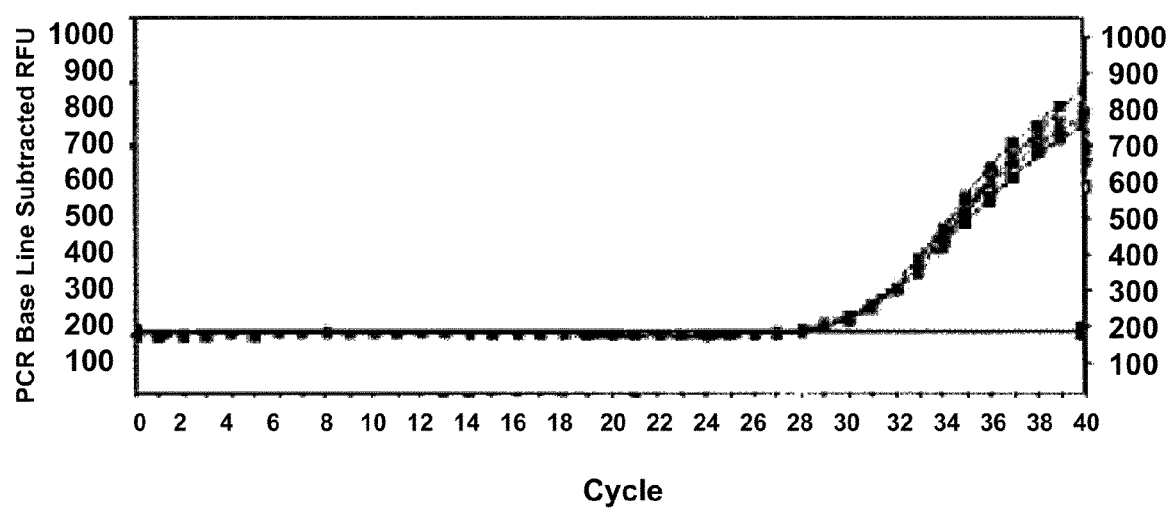
FIG. 2 shows fluorescence curves plotted as a function of PCR cycle wherein oligonucleotide probes contained a conjugated 6-carboxyfluorescein (6FAM) reporter dye and various quenchers. Fluorescence-quenched probes with 1-(phenylamino)-4(2-hydroxy-ethylamino)-anthraquinone (UQ2) (SEQ ID No: 4), 6-carboxytetramethylrhodamine (6Tamra) (SEQ ID No: 5), and N,N'-dimethyl-N,N'-diphenyl-4-((5-t-butoxycarbonylaminopentyl)aminocarbonyl)piperidinylsulfonerhodamine (QSY7) (SEQ ID No: 6) were compared in reactions containing about 10.sup.3 target DNA molecules. The log of relative fluorescence units (Y-axis) are plotted against PCR cycle number (X-axis). The curves are indistinguishable and are not individually labeled.

Relative fluorescence levels collected during PCR for each probe were graphically plotted against cycle number and are shown in FIG. 2. All curves superimposed and could not be distinguished, indicating that each of the 3 quenching groups tested were suitable quenchers for the fluorescein (6FAM) reporter dye. This example demonstrates that probe compositions comprising the new anthraquinone quenchers of the invention perform well in a quantitative real-time PCR assay and are functionally equivalent to probes that contain other quencher moieties.

Additional fluorescence-quenched probes were synthesized having a TEXAS RED® (TR) reporter dye (SEQ ID No. 7) and a Cy5 reporter dye (SEQ ID No. 8) and the anthraquinone quencher. TEXAS RED® probes could not be made using 6Tamra quencher as was previously done for the 6Fam probe (SEQ ID NO 5) because 6Tamra does not quench the TR reporter dye. Cy5 probes could not be made using either 6Tamra or QSY7 quencher as neither group will quench the Cy5 reporter dye.

Figure 3:
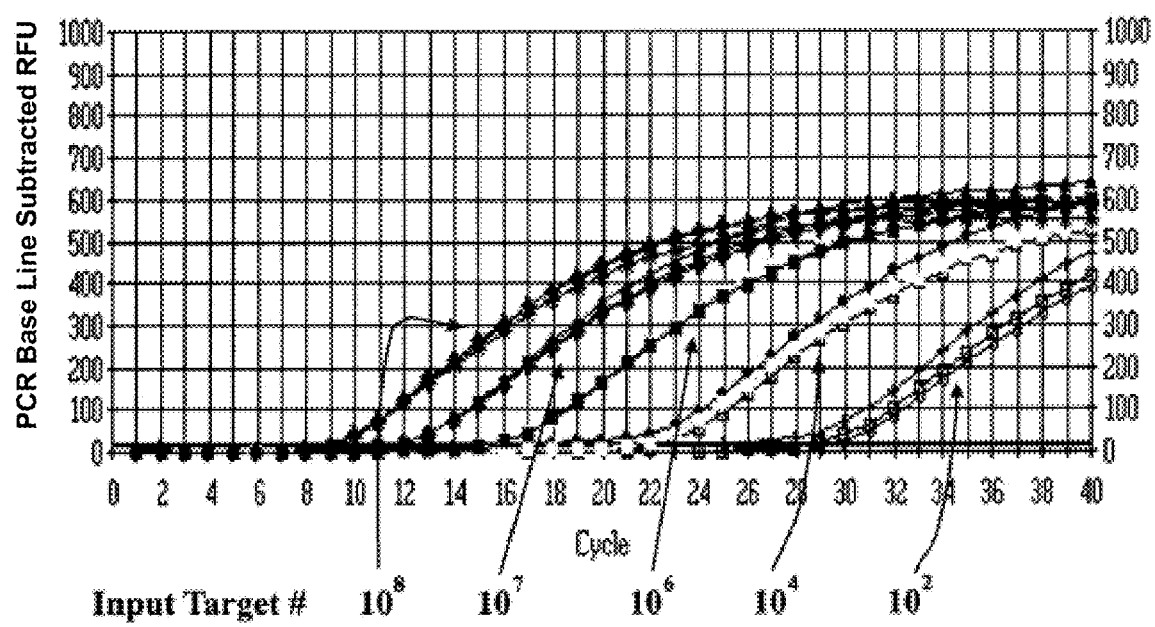
FIG. 3 shows fluorescence curves which were generated using 1H,5H,11H,15H-Xantheno[2,3,4-ij:5,6,7-i'j']diquinolizin-18-ium, 9-[2(or 4)-[[[6-[2,5-dioxo-1-pyrrolidinyl)ozy]-6-oxohexyl]amino]sulfonyl]-4(or 2)-sulfophenyl]-2,3,6,7,12,13,16,17-octahydro-inner salt (TEXAS RED® (TR)) reporter dye and UQ2 anthraquinone quencher. The probe (SEQ ID No: 7) was used with varying amounts of input target DNA molecules as indicated. Relative fluorescence units (Y-axis) are plotted against PCR cycle number (X-axis).
Figure 4:
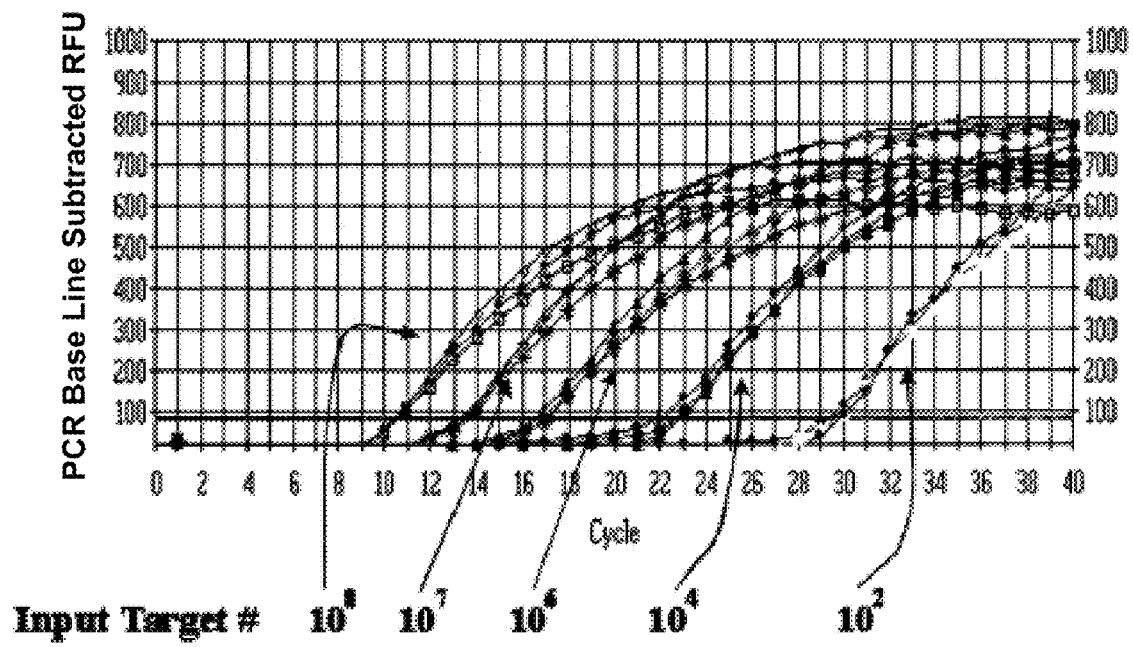
FIG. 4 shows fluorescence curves generated using indodicarbocyanine 5 (Cy5) reporter dye and UQ2 quencher as in FIG. 3. The probe (SEQ ID No: 8) was used with varying input target DNA molecules as indicated. Relative fluorescence units (Y-axis) are plotted against PCR cycle number (X-axis).

PCR reactions were carried out as described above except that multiple concentrations of target (SEQ ID No: 11) were assayed and only a single probe was tested in a given experiment (SEQ ID Nos. 7 or 8). A dilution series of input target DNA was made to include 1.times.10.sup.8, 1.times.10.sup.7, 1.times.10.sup.6, 1.times.10.sup.4, and 1.times.10.sup.2 copies of target. All data points were performed in triplicate. Cycling conditions employed were as follows: 50° C. for 2 min and 95° C. for 10 min followed by 40 cycles of 2-step PCR with 95° C. for 15 sec and 60° C. for 1 min. PCR and fluorescence measurements were done using a BioRad iCycler IQ™ Real-time PCR Detection System (Bio-Rad Laboratories, Hercules, Calif.). For the TEXAS RED® probe, a 575 nm (30 nm bandpass) excitation filter and a 625 nm (30 nm bandpass) detection filter were used. Results are shown in FIG. 3 for the TEXAS RED® probe (SEQ ID No. 7). For the Cy5 probe, a 635 nm (30 nm bandpass) excitation filter and a 680 nm (30 nm bandpass) detection filter were used. Results are shown in FIG. 4 for the Cy5 probe (SEQ ID No. 8).

These results demonstrate that the new anthraquinone quencher is useful with red (TEXAS RED®, emission 610 nm) and far-red dyes (Cy5, emission 667 nm). Further, use of the anthraquinone quencher enables use of far-red reporter dyes like Cy5 as fluorescent dyes in this range are not effectively quenched in linear probe configuration by other existing quencher groups.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better describe the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound comprising an oligonucleotide labeled with a fluorophore and quencher, wherein the oligonucleotide is adapted to hybridize to a selected nucleic acid sequence, and wherein the quencher is a di-alpha amino anthraquinone comprising a first amino group and a second amino group attached at alpha-positions of the anthraquinone, wherein fluorescence of the fluorophore is reduced by fluorescence resonance energy transfer to the quencher or by ground state quenching by the quencher when the oligonucleotide is not hybridized to the selected nucleic acid sequence.

2. The compound of claim 1, wherein the fluorophore is selected from the group consisting of pyrene, anthracene, naphthalene, acridine, stilbene, indole, benzindole, oxazole, thiazole, benzothiazole, cyanine, carbocyanine, salicylate, anthranilate, coumarin, fluorescein and rhodamine.

3. The compound of claim 1, wherein at least one of the first and second amino group is substituted with substituent comprising an aryl or an alkyl.

4. The compound of claim 1, wherein fluorescence is reduced by fluorescence resonance energy transfer when the oligonucleotide is not hybridized to the selected nucleic acid sequence.

5. The compound of claim 1, wherein fluorescence is reduced by ground state quenching when the oligonucleotide is not hybridized to the selected nucleic acid sequence.

6. The compound of claim 1, wherein fluorescence is reduced by both fluorescence resonance energy transfer and ground state quenching when the oligonucleotide is not hybridized to the selected nucleic acid sequence.

* * * * *

```
                        SEQUENCE LISTING

<160> NUMBER OF SEQ ID NOS: 11

<210> SEQ ID NO 1
<211> LENGTH: 12
<212> TYPE: DNA
<213> ORGANISM: Artificial Sequence
<220> FEATURE:
<223> OTHER INFORMATION: UQ2 Anthraquinone Labeled Oligonucleotide
<220> FEATURE:
<221> NAME/KEY: misc_feature
<223> OTHER INFORMATION: Anthraquinone Quencher UQ2 is incorporated at
      3' end of oligonucleotide

<400> SEQUENCE: 1
cagagtacct ga                                                       12

<210> SEQ ID NO 2
<211> LENGTH: 12
<212> TYPE: DNA
<213> ORGANISM: Artificial Sequence
<220> FEATURE:
<223> OTHER INFORMATION: Dark Quencher QSY7 Labeled Oligonucleotide
<220> FEATURE:
<221> NAME/KEY: misc_feature
<223> OTHER INFORMATION: Dark Quencher QSY7 is incorporated at 3' end of
      oligonucleotide

<400> SEQUENCE: 2
cagagtacct ga                                                       12

<210> SEQ ID NO 3
<211> LENGTH: 12
<212> TYPE: DNA
<213> ORGANISM: Artificial Sequence
<220> FEATURE:
<223> OTHER INFORMATION: Dark Quencher Dabcyl Labeled Oligonucleotide
<220> FEATURE:
<221> NAME/KEY: misc_feature
<223> OTHER INFORMATION: Dabcyl is incorporated at 3' end of
      oligonucleotide

<400> SEQUENCE: 3
cagagtacct ga                                                       12

<210> SEQ ID NO 4
<211> LENGTH: 20
<212> TYPE: DNA
<213> ORGANISM: Artificial Sequence
<220> FEATURE:
```

```
<223> OTHER INFORMATION: Oligonucleotide Dual-labeled Probe
<220> FEATURE:
<221> NAME/KEY: misc_feature
<223> OTHER INFORMATION: 6 FAM Reporter Dye is incorporated at 5' end of
      oligonucleotide
<220> FEATURE:
<221> NAME/KEY: misc_feature
<223> OTHER INFORMATION: UQ2 is incorporated at 3' end of
      oligonucleotide

<400> SEQUENCE: 4
acccgttcac cctcccccag                                                    20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide Dual-labeled Probe
<220> FEATURE:
<221> NAME/KEY: misc_feature
<223> OTHER INFORMATION: 6 FAM Reporter Dye is incorporated at 5' end of
      oligonucleotide
<220> FEATURE:
<221> NAME/KEY: misc_feature
<223> OTHER INFORMATION: 6 TAMRA is incorporated at 3' end of
      oligonucleotide

<400> SEQUENCE: 5
acccgttcac cctcccccag                                                    20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide Dual-labeled Probe
<220> FEATURE:
<221> NAME/KEY: misc_feature
<223> OTHER INFORMATION: 6 FAM Reporter Dye is incorporated at 5' end of
      oligonucleotide
<220> FEATURE:
<221> NAME/KEY: misc_feature
<223> OTHER INFORMATION: Dark Quencher QSY7 is incorporated at 3' end of
      oligonucleotide

<400> SEQUENCE: 6
acccgttcac cctcccccag                                                    20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide Dual-labeled Probe
<220> FEATURE:
<221> NAME/KEY: misc_feature
<223> OTHER INFORMATION: TR Reporter Dye is incorporated at 5' end of
      oligonucleotide
<220> FEATURE:
<221> NAME/KEY: misc_feature
<223> OTHER INFORMATION: Anthraquinone Quencher UQ2 is incorporated at
      3' end of oligonucleotide

<400> SEQUENCE: 7
acccgttcac cctcccccag                                                    20

<210> SEQ ID NO 8
<211> LENGTH: 20
<212> TYPE: DNA
<213> ORGANISM: Artificial Sequence
<220> FEATURE:
```

```
-continued

<223> OTHER INFORMATION: Oligonucleotide Dual-labeled Probe
<220> FEATURE:
<221> NAME/KEY: misc_feature
<223> OTHER INFORMATION: Cy5 Reporter Dye is incorporated at 5' end of
      oligonucleotide
<220> FEATURE:
<221> NAME/KEY: misc_feature
<223> OTHER INFORMATION: Anthraquinone Quencher UQ2 is incorporated at
      3' end of oligonucleotide

<400> SEQUENCE: 8
acccgttcac cctcccccag                                             20

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide Sequence Coding for Forward
      Primer

<400> SEQUENCE: 9
cagaaggtta tatctgccat cg                                          22

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide Sequence Coding for Reverse
      Primer

<400> SEQUENCE: 10
ctcaaagggt ggttcgttct ct                                          22

<210> SEQ ID NO 11
<211> LENGTH: 220
<212> TYPE: DNA
<213> ORGANISM: Artificial Sequence
<220> FEATURE:
<223> OTHER INFORMATION: Target Amplicon

<400> SEQUENCE: 11
cagaaggtta tcatctgcca tcgaggcacc cgttcaccct ccccagtga cccggattat   60 ggtctccctc ctcttgcagg gcactctctt tcctggactg atgaaaaaca gctcaaagaa  120
caaaatatca tccgtacagc taaagtgtgg accccagagg accccagaaa actcaacagt  180
caaatctttc gacaacatag agaacgaacc acctttgag                        220
```